United States Patent
Tsai et al.

(10) Patent No.: US 12,351,645 B2
(45) Date of Patent: Jul. 8, 2025

(54) ANTI-CARBONIC ANHYDRASE IX ANTIBODY

(71) Applicant: NAVI BIO-THERAPEUTICS, INC., Kaohsiung (TW)

(72) Inventors: Bor-Yu Tsai, New Taipei (TW); Wei-Ting Hsu, Taipei (TW)

(73) Assignee: NAVI BIO-THERAPEUTICIS, INC., Kaohsiung (TW)

( * ) Notice: Subject to any disclaimer, the term of this patent is extended or adjusted under 35 U.S.C. 154(b) by 561 days.

(21) Appl. No.: 17/051,635

(22) PCT Filed: May 6, 2019

(86) PCT No.: PCT/US2019/030807
§ 371 (c)(1),
(2) Date: Oct. 29, 2020

(87) PCT Pub. No.: WO2020/226612
PCT Pub. Date: Nov. 12, 2020

(65) Prior Publication Data
US 2022/0049012 A1    Feb. 17, 2022

(51) Int. Cl.
*C07K 16/30* (2006.01)
*A61P 35/00* (2006.01)
*C07K 16/40* (2006.01)

(52) U.S. Cl.
CPC .............. *C07K 16/30* (2013.01); *C07K 16/40* (2013.01); *C07K 2317/34* (2013.01); *C07K 2317/622* (2013.01); *C07K 2317/92* (2013.01); *C12Y 402/01001* (2013.01)

(58) Field of Classification Search
None
See application file for complete search history.

(56) References Cited

U.S. PATENT DOCUMENTS

| | | |
|---|---|---|
| 2004/0018198 A1 | 1/2004 | Gudas et al. |
| 2005/0031623 A1 | 2/2005 | Pastorek et al. |
| 2009/0068095 A1 | 3/2009 | Marasco et al. |
| 2013/0022640 A1 | 1/2013 | Hurwitz et al. |
| 2016/0289337 A1 | 10/2016 | Abrahmsén et al. |
| 2018/0030147 A1 | 2/2018 | Marasco et al. |
| 2018/0072813 A1 | 3/2018 | Marasco et al. |
| 2018/0186893 A1 | 7/2018 | Lenferink et al. |

FOREIGN PATENT DOCUMENTS

| | | |
|---|---|---|
| CN | 108064251 A | 5/2018 |
| JP | 2005535601 A | 11/2005 |
| WO | 03100029 A2 | 12/2003 |
| WO | 2003100029 A2 | 12/2003 |
| WO | 2004017923 A2 | 3/2004 |
| WO | 2011139375 A1 | 11/2011 |
| WO | 2012072788 A1 | 6/2012 |
| WO | 2016100980 A1 | 6/2016 |
| WO | 2016199097 A1 | 12/2016 |
| WO | 2017048850 A1 | 3/2017 |
| WO | 2017189964 A2 | 11/2017 |

OTHER PUBLICATIONS

Rudikoff et al., (PNAS 79: 1979-1983, 1982) (Year: 1982).*
Paul, Fundamental Immunology, (textbook), 292-295, 1993 (Year: 1993).*
Colman P. M. (Research in Immunology, 145:33-36, 1994) (Year: 1994).*
Brummell et al. (Biochemistry 32:1180-1187 1993) (Year: 1993).*
A549, A549 cell—Wikipedia downloaded on Aug. 18, 2024, pp. 1-3 (Year: 2024).*
Office Action with Search Report issued in Chinese patent application No. 2019800961438 on Jan. 10, 2024.
Ahlskog, JKJ et al., "Human monoclonal antibodies targeting carbonic anhydrase IX for the molecular imaging of hypoxic regions in solid tumours", British Journal of Cancer, vol. 101, No. 4, Jul. 21, 2009 (Jul. 21, 2009), pp. 645-657, XP055014314, ISSN: 0007-0920, DOI: 10.1038/sj.bjc.6605200.
Araste, Fatemeh et al., "A novel VHH nanobody against the active site (the CA domain) of tumor-associated, carbonic anhydrase isoform IX and its usefulness for cancer diagnosis", Biotechnology Letters, vol. 36, No. 1, Sep. 26, 2013 (Sep. 26, 2013), pp. 21-28, XP055650437, Dordrecht ISSN: 0141-5492, DOI: 10.1007/S10529-013-1340-1.
Mboge, Mam Y. et al. "Advances in Anti-Cancer Drug Development Targeting Carbonic Anhydrase IX and XII" In: "Topics in Anti-Cancer Research", Dec. 18, 2016 (Dec. 18, 2016), Bentham Science Publishers, XP055596596, ISBN: 978-1-68108-333-9 pp. 3-42, DOI: 10.2174/9781681083339116050004.
Murri-Plesko, Margarita T. et al. "Antibody inhibiting enzymatic activity of tumour-associated carbonic anhydrase isoform IX", European Journal of Pharmacology, Elsevier Science, NL, vol. 657, No. 1, Jan. 27, 2011 (Jan. 27, 2011), pp. 173-183, XP028175257, ISSN: 0014-2999, DOI: 10.1016/J.EJPHAR.2011.01.063 [retrieved on Feb. 10, 2011].
Office Action issued in European Patent Application No. 19928127.0 on Oct. 18, 2022.
Office Action issued in Japan Patent Application No. 2021-566230 on Mar. 7, 2023. English Machine Translation Included.
Xu, Chen et al, "Unique Biological Properties of Catalytic Domain Directed Human Anti-CAIX Antibodies Discovered through Phage-Display Technology", PLOS ONE, vol. 5, No. 3, Mar. 10, 2010 (Mar. 10, 2010), p. e9625, XP055259684, DOI: 10.1371/journal.pone.0009625.

(Continued)

*Primary Examiner* — Kimberly Ballard
*Assistant Examiner* — Aditi Dutt
(74) *Attorney, Agent, or Firm* — Prosyla Group PC

(57) ABSTRACT

The present invention relates to epitopes located in CAIX and anti-CAIX antibodies having binding activity with cancer cells. The present invention also relates to the composition and application of the CAIX epitopes and anti-CAIX antibodies in the diagnosis, prevention and/or treatment of cancers.

18 Claims, 7 Drawing Sheets

Specification includes a Sequence Listing.

(56) References Cited

OTHER PUBLICATIONS

Zatovicova, M. et al., "Carbonic Anhydrase IX as an Anticancer Therapy Target: Preclinical Evaluation of Internalizing Monoclonal Antibody Directed to Catalytic Domain", Current Pharmaceutical Design, vol. 16, No. 29, Oct. 1, 2010 (Oct. 1, 2010), pp. 3255-3263, XP055650435, NL ISSN: 1381-6128, DOI: 10.2174/138161210793429832.

Zatovicova, Miriam et al, "Monoclonal antibody G250 targeting CA IX: Binding specificity, internalization and therapeutic effects in a non-renal cancer model", International Journal of Oncology, vol. 45, No. 6, Sep. 17, 2014 (Sep. 17, 2014), pp. 2455-2467, XP055650450, GR ISSN: 1019-6439, DOI: 10.3892/ijo.2014.2658.

* cited by examiner

SEQUENCE LISTING

```
<160> NUMBER OF SEQ ID NOS: 66

<210> SEQ ID NO 1
<211> LENGTH: 8
<212> TYPE: PRT
<213> ORGANISM: artificial sequence
<220> FEATURE:
<223> OTHER INFORMATION: synthetic peptide

<400> SEQUENCE: 1

Ser Gly Ser Ser Gly Ser Tyr Gly
1               5

<210> SEQ ID NO 2
<211> LENGTH: 7
<212> TYPE: PRT
<213> ORGANISM: artificial sequence
<220> FEATURE:
<223> OTHER INFORMATION: synthetic peptide

<400> SEQUENCE: 2

Tyr Asn Asp Lys Arg Pro Ser
1               5

<210> SEQ ID NO 3
<211> LENGTH: 10
<212> TYPE: PRT
<213> ORGANISM: artificial sequence
<220> FEATURE:
<223> OTHER INFORMATION: synthetic peptide

<400> SEQUENCE: 3
```

```
Gly Ser Ala Asp Arg Ser Gly Ala Gly Ile
1               5                   10

<210> SEQ ID NO 4
<211> LENGTH: 8
<212> TYPE: PRT
<213> ORGANISM: artificial sequence
<220> FEATURE:
<223> OTHER INFORMATION: synthetic peptide

<400> SEQUENCE: 4

Ser Gly Ser Arg Gly Ser Tyr Gly
1               5

<210> SEQ ID NO 5
<211> LENGTH: 7
<212> TYPE: PRT
<213> ORGANISM: artificial sequence
<220> FEATURE:
<223> OTHER INFORMATION: synthetic peptide

<400> SEQUENCE: 5

Tyr Asn Val Lys Arg Pro Ser
1               5

<210> SEQ ID NO 6
<211> LENGTH: 8
<212> TYPE: PRT
<213> ORGANISM: artificial sequence
<220> FEATURE:
<223> OTHER INFORMATION: synthetic peptide

<400> SEQUENCE: 6

Ser Gly Gly Gly Lys Asn Tyr Gly
1               5

<210> SEQ ID NO 7
<211> LENGTH: 7
<212> TYPE: PRT
<213> ORGANISM: artificial sequence
<220> FEATURE:
<223> OTHER INFORMATION: synthetic peptide

<400> SEQUENCE: 7

Leu Asn Asp Lys Arg Pro Ser
1               5

<210> SEQ ID NO 8
<211> LENGTH: 8
<212> TYPE: PRT
<213> ORGANISM: artificial sequence
<220> FEATURE:
<223> OTHER INFORMATION: synthetic peptide

<400> SEQUENCE: 8

Gly Ser Arg Asp Ser Ser Pro Thr
1               5

<210> SEQ ID NO 9
<211> LENGTH: 5
<212> TYPE: PRT
<213> ORGANISM: artificial sequence
<220> FEATURE:
<223> OTHER INFORMATION: synthetic peptide

<400> SEQUENCE: 9
```

```
Ser His Gly Met Ala
1               5

<210> SEQ ID NO 10
<211> LENGTH: 17
<212> TYPE: PRT
<213> ORGANISM: artificial sequence
<220> FEATURE:
<223> OTHER INFORMATION: synthetic peptide

<400> SEQUENCE: 10

Gly Ile Ser Asn Thr Gly Arg Tyr Thr Asn Tyr Gly Ser Ala Val Lys
1               5                   10                  15

Gly

<210> SEQ ID NO 11
<211> LENGTH: 15
<212> TYPE: PRT
<213> ORGANISM: artificial sequence
<220> FEATURE:
<223> OTHER INFORMATION: synthetic peptide

<400> SEQUENCE: 11

Ala Ala Val Asn Cys Val Tyr Gly Cys Pro Gly Ser Ile Asp Ala
1               5                   10                  15

<210> SEQ ID NO 12
<211> LENGTH: 5
<212> TYPE: PRT
<213> ORGANISM: artificial sequence
<220> FEATURE:
<223> OTHER INFORMATION: synthetic peptide

<400> SEQUENCE: 12

Ser Tyr Ala Ile Gln
1               5

<210> SEQ ID NO 13
<211> LENGTH: 17
<212> TYPE: PRT
<213> ORGANISM: artificial sequence
<220> FEATURE:
<223> OTHER INFORMATION: synthetic peptide

<400> SEQUENCE: 13

Gly Ile Ser Asp Asp Gly Ser Trp Thr Gly Tyr Gly Ala Ala Val Lys
1               5                   10                  15

Gly

<210> SEQ ID NO 14
<211> LENGTH: 20
<212> TYPE: PRT
<213> ORGANISM: artificial sequence
<220> FEATURE:
<223> OTHER INFORMATION: synthetic peptide

<400> SEQUENCE: 14

Gly Ala Gly Thr Gly Tyr Cys Ala Asn Arg Ser Phe Gly Cys Ala Ser
1               5                   10                  15

Thr Ile Asp Ala
            20

<210> SEQ ID NO 15
<211> LENGTH: 5
<212> TYPE: PRT
```

```
<213> ORGANISM: artificial sequence
<220> FEATURE:
<223> OTHER INFORMATION: synthetic peptide

<400> SEQUENCE: 15

Ser Phe Asn Met Phe
1               5

<210> SEQ ID NO 16
<211> LENGTH: 17
<212> TYPE: PRT
<213> ORGANISM: artificial sequence
<220> FEATURE:
<223> OTHER INFORMATION: synthetic peptide

<400> SEQUENCE: 16

Ala Ile Ser Ser Asp Gly Ser Arg Ser Arg Tyr Gly Ser Ala Val Gln
1               5                   10                  15

Gly

<210> SEQ ID NO 17
<211> LENGTH: 20
<212> TYPE: PRT
<213> ORGANISM: artificial sequence
<220> FEATURE:
<223> OTHER INFORMATION: synthetic peptide

<400> SEQUENCE: 17

Arg Pro Tyr Ser Gly Cys Thr Ser Asn Asn Phe Cys Phe Asn Ala Ala
1               5                   10                  15

Tyr Ile Asp Val
            20

<210> SEQ ID NO 18
<211> LENGTH: 5
<212> TYPE: PRT
<213> ORGANISM: artificial sequence
<220> FEATURE:
<223> OTHER INFORMATION: synthetic peptide

<400> SEQUENCE: 18

Ser Tyr Ala Met Asn
1               5

<210> SEQ ID NO 19
<211> LENGTH: 17
<212> TYPE: PRT
<213> ORGANISM: artificial sequence
<220> FEATURE:
<223> OTHER INFORMATION: synthetic peptide

<400> SEQUENCE: 19

Gly Ile Thr Asn Thr Gly Ser Ser Ala Gly Tyr Gly Ala Ala Val Lys
1               5                   10                  15

Gly

<210> SEQ ID NO 20
<211> LENGTH: 17
<212> TYPE: PRT
<213> ORGANISM: artificial sequence
<220> FEATURE:
<223> OTHER INFORMATION: synthetic peptide

<400> SEQUENCE: 20

Ser Tyr Gly Gly Trp Cys Asp His Ala Cys Ala Pro Asp Asp Ile Asp
```

-continued

```
1               5                   10                  15
Thr

<210> SEQ ID NO 21
<211> LENGTH: 103
<212> TYPE: PRT
<213> ORGANISM: artificial sequence
<220> FEATURE:
<223> OTHER INFORMATION: synthetic polypeptide

<400> SEQUENCE: 21

Ala Leu Thr Gln Pro Ser Ser Val Ser Ala Asn Leu Gly Glu Thr Val
1               5                   10                  15

Glu Ile Thr Cys Ser Gly Ser Ser Gly Ser Tyr Gly Trp Tyr Gln Gln
            20                  25                  30

Lys Ser Pro Gly Ser Ala Pro Val Thr Val Ile Tyr Tyr Asn Asp Lys
        35                  40                  45

Arg Pro Ser Asp Ile Pro Ser Arg Phe Ser Gly Ser Lys Ser Gly Ser
    50                  55                  60

Thr Gly Thr Leu Thr Ile Thr Gly Val Gln Ala Glu Asp Glu Ala Val
65                  70                  75                  80

Tyr Tyr Cys Gly Ser Ala Asp Arg Ser Gly Ala Gly Ile Phe Gly Ala
                85                  90                  95

Gly Thr Thr Leu Thr Val Leu
            100

<210> SEQ ID NO 22
<211> LENGTH: 103
<212> TYPE: PRT
<213> ORGANISM: artificial sequence
<220> FEATURE:
<223> OTHER INFORMATION: synthetic polypeptide

<400> SEQUENCE: 22

Ala Leu Thr Gln Pro Ser Ser Val Ser Ala Asn Leu Gly Glu Thr Val
1               5                   10                  15

Glu Ile Thr Cys Ser Gly Ser Arg Gly Ser Tyr Gly Trp Tyr Gln Gln
            20                  25                  30

Lys Ser Pro Gly Ser Ala Pro Val Thr Val Ile Tyr Tyr Asn Val Lys
        35                  40                  45

Arg Pro Ser Asp Ile Pro Ser Arg Phe Ser Gly Ser Lys Ser Gly Ser
    50                  55                  60

Thr Gly Thr Leu Thr Ile Thr Gly Val Gln Ala Glu Asp Glu Ala Val
65                  70                  75                  80

Tyr Tyr Cys Gly Ser Ala Asp Arg Ser Gly Ala Gly Ile Phe Gly Ala
                85                  90                  95

Gly Thr Thr Leu Thr Val Leu
            100

<210> SEQ ID NO 23
<211> LENGTH: 101
<212> TYPE: PRT
<213> ORGANISM: artificial sequence
<220> FEATURE:
<223> OTHER INFORMATION: synthetic polypeptide

<400> SEQUENCE: 23

Ala Leu Thr Gln Pro Ser Ser Val Ser Ala Asn Pro Gly Glu Thr Val
1               5                   10                  15
```

```
Lys Ile Thr Cys Ser Gly Gly Lys Asn Tyr Gly Trp Tyr Gln Gln
            20                  25                  30

Lys Ser Pro Gly Ser Ala Pro Val Thr Val Ile Tyr Leu Asn Asp Lys
        35                  40                  45

Arg Pro Ser Asn Ile Pro Ser Arg Phe Ser Gly Ser Lys Ser Gly Ser
    50                  55                  60

Thr His Thr Leu Thr Ile Thr Gly Val Gln Ala Glu Asp Glu Ala Val
65                  70                  75                  80

Tyr Phe Cys Gly Ser Arg Asp Ser Ser Pro Thr Phe Gly Ala Gly Thr
                85                  90                  95

Thr Leu Thr Val Leu
            100
```

<210> SEQ ID NO 24
<211> LENGTH: 124
<212> TYPE: PRT
<213> ORGANISM: artificial sequence
<220> FEATURE:
<223> OTHER INFORMATION: synthetic polypeptide

<400> SEQUENCE: 24

```
Ala Val Thr Leu Asp Glu Pro Gly Gly Leu Gln Thr Pro Gly Gly
1               5                   10                  15

Thr Leu Ser Leu Val Cys Lys Ala Ser Gly Phe Asp Ile Ser Ser His
            20                  25                  30

Gly Met Ala Trp Val Arg Gln Ala Pro Gly Lys Gly Leu Glu Tyr Val
        35                  40                  45

Ala Gly Ile Ser Asn Thr Gly Arg Tyr Thr Asn Tyr Gly Ser Ala Val
    50                  55                  60

Lys Gly Arg Ala Thr Ile Ser Arg Asp Asn Gly Gln Ser Thr Val Arg
65                  70                  75                  80

Leu Gln Leu Asn Asp Leu Arg Ala Glu Asp Ala Gly Thr Tyr Phe Cys
                85                  90                  95

Ala Arg Ala Ala Val Asn Cys Val Tyr Gly Cys Pro Gly Ser Ile Asp
            100                 105                 110

Ala Trp Gly Leu Gly Thr Glu Val Ile Val Ser Ser
        115                 120
```

<210> SEQ ID NO 25
<211> LENGTH: 129
<212> TYPE: PRT
<213> ORGANISM: artificial sequence
<220> FEATURE:
<223> OTHER INFORMATION: synthetic polypeptide

<400> SEQUENCE: 25

```
Ala Val Thr Leu Asp Glu Ser Gly Gly Gly Leu Gln Thr Pro Gly Gly
1               5                   10                  15

Gly Leu Ser Leu Val Cys Lys Ala Ser Gly Phe Thr Phe Ser Ser Tyr
            20                  25                  30

Ala Ile Gln Trp Val Arg Gln Ala Pro Gly Lys Gly Leu Glu Trp Val
        35                  40                  45

Ala Gly Ile Ser Asp Asp Gly Ser Trp Thr Gly Tyr Gly Ala Ala Val
    50                  55                  60

Lys Gly Arg Ala Thr Ile Ser Arg Asp Asn Gly Gln Ser Thr Met Arg
65                  70                  75                  80

Leu Gln Leu Asn Asn Leu Arg Ala Glu Asp Thr Gly Ile Tyr Tyr Cys
                85                  90                  95
```

```
Ala Lys Gly Ala Gly Thr Gly Tyr Cys Ala Asn Arg Ser Phe Gly Cys
            100                 105                 110

Ala Ser Thr Ile Asp Ala Trp Gly His Gly Thr Glu Val Ile Val Ser
            115                 120                 125

Ser
```

<210> SEQ ID NO 26
<211> LENGTH: 129
<212> TYPE: PRT
<213> ORGANISM: artificial sequence
<220> FEATURE:
<223> OTHER INFORMATION: synthetic polypeptide

<400> SEQUENCE: 26

```
Ala Val Thr Leu Asp Glu Ser Gly Gly Leu Gln Thr Pro Gly Gly
1               5                   10                  15

Ala Leu Ser Leu Val Cys Lys Ala Ser Gly Phe Thr Phe Ser Ser Phe
            20                  25                  30

Asn Met Phe Trp Val Arg Gln Ala Pro Gly Lys Gly Leu Glu Tyr Val
        35                  40                  45

Ala Ala Ile Ser Ser Asp Gly Ser Arg Ser Arg Tyr Gly Ser Ala Val
    50                  55                  60

Gln Gly Arg Ala Thr Ile Ser Arg Asp Asn Gly Gln Ser Thr Val Arg
65                  70                  75                  80

Leu Gln Leu Asn Ser Leu Arg Ala Glu Asp Thr Gly Thr Tyr Tyr Cys
                85                  90                  95

Ala Lys Arg Pro Tyr Ser Gly Cys Thr Ser Asn Asn Phe Cys Phe Asn
            100                 105                 110

Ala Ala Tyr Ile Asp Val Trp Gly His Gly Thr Glu Val Ile Val Ser
            115                 120                 125

Ser
```

<210> SEQ ID NO 27
<211> LENGTH: 126
<212> TYPE: PRT
<213> ORGANISM: artificial sequence
<220> FEATURE:
<223> OTHER INFORMATION: synthetic polypeptide

<400> SEQUENCE: 27

```
Ala Val Thr Leu Asp Glu Ser Glu Gly Gly Leu Gln Thr Pro Gly Gly
1               5                   10                  15

Ala Leu Ser Leu Val Cys Lys Ala Ser Gly Phe Thr Phe Ser Ser Tyr
            20                  25                  30

Ala Met Asn Trp Val Arg Gln Ala Pro Gly Lys Gly Leu Glu Phe Val
        35                  40                  45

Ala Gly Ile Thr Asn Thr Gly Ser Ser Ala Gly Tyr Gly Ala Ala Val
    50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Ala Thr Tyr Phe Cys
                85                  90                  95

Thr Lys Ser Tyr Gly Gly Trp Cys Asp His Ala Cys Ala Pro Asp Asp
            100                 105                 110

Ile Asp Thr Trp Gly His Gly Thr Glu Val Ile Val Ser Ser
            115                 120                 125
```

<210> SEQ ID NO 28
<211> LENGTH: 129
<212> TYPE: PRT
<213> ORGANISM: artificial sequence
<220> FEATURE:
<223> OTHER INFORMATION: synthetic polypeptide

<400> SEQUENCE: 28

Ala Val Thr Leu Asp Glu Ser Gly Gly Gly Leu Gln Thr Pro Arg Gly
1               5                   10                  15

Ala Leu Ser Leu Val Cys Lys Ala Ser Gly Phe Thr Phe Ser Ser Phe
            20                  25                  30

Asn Met Phe Trp Val Arg Gln Ala Pro Gly Lys Gly Leu Glu Tyr Val
        35                  40                  45

Ala Ala Ile Ser Ser Asp Gly Ser Arg Ser Arg Tyr Gly Ser Ala Val
    50                  55                  60

Gln Gly Arg Ala Thr Ile Ser Arg Asp Asn Gly Gln Ser Thr Val Arg
65                  70                  75                  80

Leu Gln Leu Asn Ser Leu Arg Ala Glu Asp Thr Gly Thr Tyr Tyr Cys
                85                  90                  95

Ala Lys Arg Pro Tyr Ser Gly Cys Thr Ser Asn Asn Phe Cys Phe Asn
            100                 105                 110

Ala Ala Tyr Ile Asp Val Trp Gly His Gly Thr Glu Val Ile Val Ser
        115                 120                 125

Ser

<210> SEQ ID NO 29
<211> LENGTH: 7
<212> TYPE: PRT
<213> ORGANISM: artificial sequence
<220> FEATURE:
<223> OTHER INFORMATION: synthetic peptide

<400> SEQUENCE: 29

Gly Gln Ser Ser Arg Ser Ser
1               5

<210> SEQ ID NO 30
<211> LENGTH: 18
<212> TYPE: PRT
<213> ORGANISM: artificial sequence
<220> FEATURE:
<223> OTHER INFORMATION: synthetic peptide

<400> SEQUENCE: 30

Gly Gln Ser Ser Arg Ser Ser Gly Gly Ser Ser Gly Gly
1               5                   10                  15

Gly Ser

<210> SEQ ID NO 31
<211> LENGTH: 18
<212> TYPE: PRT
<213> ORGANISM: artificial sequence
<220> FEATURE:
<223> OTHER INFORMATION: synthetic peptide

<400> SEQUENCE: 31

Gly Gln Ser Ser Arg Ser Ser Gly Gly Gly Gly Ser Ser Gly Gly Gly
1               5                   10                  15

Gly Ser

```
<210> SEQ ID NO 32
<211> LENGTH: 116
<212> TYPE: PRT
<213> ORGANISM: artificial sequence
<220> FEATURE:
<223> OTHER INFORMATION: synthetic polypeptide

<400> SEQUENCE: 32

Gln Arg Leu Pro Arg Met Gln Glu Asp Ser Pro Leu Gly Gly Ser
1               5                   10                  15

Ser Gly Glu Asp Asp Pro Leu Gly Glu Asp Leu Pro Ser Glu
            20                  25                  30

Asp Ser Pro Arg Glu Glu Asp Pro Gly Glu Asp Leu Pro Gly
                35                  40                  45

Glu Glu Asp Leu Pro Gly Glu Glu Asp Leu Pro Glu Val Lys Pro Lys
50                  55                  60

Ser Glu Glu Glu Gly Ser Leu Lys Leu Glu Asp Leu Pro Thr Val Glu
65                  70                  75                  80

Ala Pro Gly Asp Pro Gln Glu Pro Gln Asn Asn Ala His Arg Asp Lys
                85                  90                  95

Glu Gly Asp Asp Gln Ser His Trp Arg Tyr Gly Gly Asp Pro Pro Trp
                100                 105                 110

Pro Arg Val Ser
        115

<210> SEQ ID NO 33
<211> LENGTH: 126
<212> TYPE: PRT
<213> ORGANISM: artificial sequence
<220> FEATURE:
<223> OTHER INFORMATION: synthetic polypeptide

<400> SEQUENCE: 33

His Trp Gly Ala Ala Gly Arg Pro Gly Ser Glu His Thr Val Glu Gly
1               5                   10                  15

His Arg Phe Pro Ala Glu Ile His Val Val His Leu Ser Thr Ala Phe
                20                  25                  30

Ala Arg Val Asp Glu Ala Leu Gly Arg Pro Gly Gly Leu Ala Val Leu
                35                  40                  45

Ala Ala Phe Leu Glu Glu Gly Pro Glu Glu Asn Ser Ala Tyr Glu Gln
50                  55                  60

Leu Leu Ser Arg Leu Glu Glu Ile Ala Glu Glu Gly Ser Glu Thr Gln
65                  70                  75                  80

Val Pro Gly Leu Asp Ile Ser Ala Leu Leu Pro Ser Asp Phe Ser Arg
                85                  90                  95

Tyr Phe Gln Tyr Glu Gly Ser Leu Thr Thr Pro Pro Cys Ala Gln Gly
                100                 105                 110

Val Ile Trp Thr Val Phe Asn Gln Thr Val Met Leu Ser Ala
        115                 120                 125

<210> SEQ ID NO 34
<211> LENGTH: 20
<212> TYPE: PRT
<213> ORGANISM: artificial sequence
<220> FEATURE:
<223> OTHER INFORMATION: synthetic peptide

<400> SEQUENCE: 34

Ala Leu Thr Gln Pro Ser Ser Val Ser Ala Asn Leu Gly Glu Thr Val
```

```
1               5                   10                  15

Glu Ile Thr Cys
            20

<210> SEQ ID NO 35
<211> LENGTH: 20
<212> TYPE: PRT
<213> ORGANISM: artificial sequence
<220> FEATURE:
<223> OTHER INFORMATION: synthetic peptide

<400> SEQUENCE: 35

Ala Leu Thr Gln Pro Ser Ser Val Ser Ala Asn Pro Gly Glu Thr Val
1               5                   10                  15

Lys Ile Thr Cys
            20

<210> SEQ ID NO 36
<211> LENGTH: 26
<212> TYPE: PRT
<213> ORGANISM: artificial sequence
<220> FEATURE:
<223> OTHER INFORMATION: synthetic peptide

<400> SEQUENCE: 36

Ala Ile Gln Met Thr Gln Ser Pro Ser Ser Leu Ser Ala Ser Val Gly
1               5                   10                  15

Asp Arg Val Thr Ile Thr Cys Arg Ala Ser
            20                  25

<210> SEQ ID NO 37
<211> LENGTH: 26
<212> TYPE: PRT
<213> ORGANISM: artificial sequence
<220> FEATURE:
<223> OTHER INFORMATION: synthetic peptide

<400> SEQUENCE: 37

Asp Ile Gln Met Thr Gln Ser Pro Ser Ser Leu Ser Ala Ser Val Gly
1               5                   10                  15

Asp Arg Val Thr Ile Thr Cys Ser Ala Ser
            20                  25

<210> SEQ ID NO 38
<211> LENGTH: 16
<212> TYPE: PRT
<213> ORGANISM: artificial sequence
<220> FEATURE:
<223> OTHER INFORMATION: synthetic peptide

<400> SEQUENCE: 38

Trp Tyr Gln Gln Lys Ser Pro Gly Ser Ala Pro Val Thr Val Ile Tyr
1               5                   10                  15

<210> SEQ ID NO 39
<211> LENGTH: 17
<212> TYPE: PRT
<213> ORGANISM: artificial sequence
<220> FEATURE:
<223> OTHER INFORMATION: synthetic peptide

<400> SEQUENCE: 39

Val Ala Trp Tyr Gln Gln Lys Pro Gly Lys Ala Pro Lys Leu Leu Ile
1               5                   10                  15
```

Tyr

<210> SEQ ID NO 40
<211> LENGTH: 17
<212> TYPE: PRT
<213> ORGANISM: artificial sequence
<220> FEATURE:
<223> OTHER INFORMATION: synthetic peptide

<400> SEQUENCE: 40

Leu Asn Trp Tyr Gln Gln Lys Pro Gly Lys Ala Pro Lys Val Leu Ile
1               5                   10                  15

Tyr

<210> SEQ ID NO 41
<211> LENGTH: 32
<212> TYPE: PRT
<213> ORGANISM: artificial sequence
<220> FEATURE:
<223> OTHER INFORMATION: synthetic peptide

<400> SEQUENCE: 41

Asp Ile Pro Ser Arg Phe Ser Gly Ser Lys Ser Gly Ser Thr Gly Thr
1               5                   10                  15

Leu Thr Ile Thr Gly Val Gln Ala Glu Asp Glu Ala Val Tyr Tyr Cys
                20                  25                  30

<210> SEQ ID NO 42
<211> LENGTH: 32
<212> TYPE: PRT
<213> ORGANISM: artificial sequence
<220> FEATURE:
<223> OTHER INFORMATION: synthetic peptide

<400> SEQUENCE: 42

Asn Ile Pro Ser Arg Phe Ser Gly Ser Lys Ser Gly Ser Thr His Thr
1               5                   10                  15

Leu Thr Ile Thr Gly Val Gln Ala Glu Asp Glu Ala Val Tyr Phe Cys
                20                  25                  30

<210> SEQ ID NO 43
<211> LENGTH: 32
<212> TYPE: PRT
<213> ORGANISM: artificial sequence
<220> FEATURE:
<223> OTHER INFORMATION: synthetic peptide

<400> SEQUENCE: 43

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
                20                  25                  30

<210> SEQ ID NO 44
<211> LENGTH: 10
<212> TYPE: PRT
<213> ORGANISM: artificial sequence
<220> FEATURE:
<223> OTHER INFORMATION: synthetic peptide

<400> SEQUENCE: 44

Phe Gly Ala Gly Thr Thr Leu Thr Val Leu
1               5                   10

-continued

```
<210> SEQ ID NO 45
<211> LENGTH: 10
<212> TYPE: PRT
<213> ORGANISM: artificial sequence
<220> FEATURE:
<223> OTHER INFORMATION: synthetic peptide

<400> SEQUENCE: 45

Phe Gly Gln Gly Thr Lys Val Glu Ile Lys
1               5                   10

<210> SEQ ID NO 46
<211> LENGTH: 30
<212> TYPE: PRT
<213> ORGANISM: artificial sequence
<220> FEATURE:
<223> OTHER INFORMATION: synthetic peptide

<400> SEQUENCE: 46

Ala Val Thr Leu Asp Glu Pro Gly Gly Leu Gln Thr Pro Gly Gly
1               5                   10                  15

Thr Leu Ser Leu Val Cys Lys Ala Ser Gly Phe Asp Ile Ser
            20                  25                  30

<210> SEQ ID NO 47
<211> LENGTH: 30
<212> TYPE: PRT
<213> ORGANISM: artificial sequence
<220> FEATURE:
<223> OTHER INFORMATION: synthetic peptide

<400> SEQUENCE: 47

Ala Val Thr Leu Asp Glu Ser Gly Gly Leu Gln Thr Pro Gly Gly
1               5                   10                  15

Gly Leu Ser Leu Val Cys Lys Ala Ser Gly Phe Thr Phe Ser
            20                  25                  30

<210> SEQ ID NO 48
<211> LENGTH: 30
<212> TYPE: PRT
<213> ORGANISM: artificial sequence
<220> FEATURE:
<223> OTHER INFORMATION: synthetic peptide

<400> SEQUENCE: 48

Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Thr Phe Ser
            20                  25                  30

<210> SEQ ID NO 49
<211> LENGTH: 30
<212> TYPE: PRT
<213> ORGANISM: artificial sequence
<220> FEATURE:
<223> OTHER INFORMATION: synthetic peptide

<400> SEQUENCE: 49

Ala Val Thr Leu Asp Glu Ser Glu Gly Gly Leu Gln Thr Pro Gly Gly
1               5                   10                  15

Ala Leu Ser Leu Val Cys Lys Ala Ser Gly Phe Thr Phe Ser
            20                  25                  30

<210> SEQ ID NO 50
<211> LENGTH: 30
```

```
<212> TYPE: PRT
<213> ORGANISM: artificial sequence
<220> FEATURE:
<223> OTHER INFORMATION: synthetic peptide

<400> SEQUENCE: 50

Ala Val Thr Leu Asp Glu Ser Gly Gly Gly Leu Gln Thr Pro Arg Gly
1               5                   10                  15

Ala Leu Ser Leu Val Cys Lys Ala Ser Gly Phe Thr Phe Ser
            20                  25                  30

<210> SEQ ID NO 51
<211> LENGTH: 30
<212> TYPE: PRT
<213> ORGANISM: artificial sequence
<220> FEATURE:
<223> OTHER INFORMATION: synthetic peptide

<400> SEQUENCE: 51

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ile
            20                  25                  30

<210> SEQ ID NO 52
<211> LENGTH: 30
<212> TYPE: PRT
<213> ORGANISM: artificial sequence
<220> FEATURE:
<223> OTHER INFORMATION: synthetic peptide

<400> SEQUENCE: 52

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr
            20                  25                  30

<210> SEQ ID NO 53
<211> LENGTH: 14
<212> TYPE: PRT
<213> ORGANISM: artificial sequence
<220> FEATURE:
<223> OTHER INFORMATION: synthetic peptide

<400> SEQUENCE: 53

Trp Val Arg Gln Ala Pro Gly Lys Gly Leu Glu Tyr Val Ala
1               5                   10

<210> SEQ ID NO 54
<211> LENGTH: 14
<212> TYPE: PRT
<213> ORGANISM: artificial sequence
<220> FEATURE:
<223> OTHER INFORMATION: synthetic peptide

<400> SEQUENCE: 54

Trp Val Arg Gln Ala Pro Gly Lys Gly Leu Glu Trp Val Ala
1               5                   10

<210> SEQ ID NO 55
<211> LENGTH: 14
<212> TYPE: PRT
<213> ORGANISM: artificial sequence
<220> FEATURE:
<223> OTHER INFORMATION: synthetic peptide
```

```
<400> SEQUENCE: 55

Trp Val Arg Gln Ala Pro Gly Lys Gly Leu Glu Phe Val Ala
1               5                   10

<210> SEQ ID NO 56
<211> LENGTH: 14
<212> TYPE: PRT
<213> ORGANISM: artificial sequence
<220> FEATURE:
<223> OTHER INFORMATION: synthetic peptide

<400> SEQUENCE: 56

Trp Val Arg Gln Ala Pro Gly Lys Gly Leu Glu Trp Val Gly
1               5                   10

<210> SEQ ID NO 57
<211> LENGTH: 32
<212> TYPE: PRT
<213> ORGANISM: artificial sequence
<220> FEATURE:
<223> OTHER INFORMATION: synthetic peptide

<400> SEQUENCE: 57

Arg Ala Thr Ile Ser Arg Asp Asn Gly Gln Ser Thr Val Arg Leu Gln
1               5                   10                  15

Leu Asn Asp Leu Arg Ala Glu Asp Ala Gly Thr Tyr Phe Cys Ala Arg
            20                  25                  30

<210> SEQ ID NO 58
<211> LENGTH: 32
<212> TYPE: PRT
<213> ORGANISM: artificial sequence
<220> FEATURE:
<223> OTHER INFORMATION: synthetic peptide

<400> SEQUENCE: 58

Arg Ala Thr Ile Ser Arg Asp Asn Gly Gln Ser Thr Met Arg Leu Gln
1               5                   10                  15

Leu Asn Asn Leu Arg Ala Glu Asp Thr Gly Ile Tyr Tyr Cys Ala Lys
            20                  25                  30

<210> SEQ ID NO 59
<211> LENGTH: 32
<212> TYPE: PRT
<213> ORGANISM: artificial sequence
<220> FEATURE:
<223> OTHER INFORMATION: synthetic peptide

<400> SEQUENCE: 59

Arg Ala Thr Ile Ser Arg Asp Asn Gly Gln Ser Thr Val Arg Leu Gln
1               5                   10                  15

Leu Asn Ser Leu Arg Ala Glu Asp Thr Gly Thr Tyr Tyr Cys Ala Lys
            20                  25                  30

<210> SEQ ID NO 60
<211> LENGTH: 32
<212> TYPE: PRT
<213> ORGANISM: artificial sequence
<220> FEATURE:
<223> OTHER INFORMATION: synthetic peptide

<400> SEQUENCE: 60

Arg Ala Thr Ile Ser Arg Asp Asn Gly Gln Ser Thr Val Arg Leu Gln
1               5                   10                  15
```

Leu Asn Asn Leu Arg Ala Glu Asp Thr Ala Thr Tyr Phe Cys Thr Lys
            20                  25                  30

<210> SEQ ID NO 61
<211> LENGTH: 32
<212> TYPE: PRT
<213> ORGANISM: artificial sequence
<220> FEATURE:
<223> OTHER INFORMATION: synthetic peptide

<400> SEQUENCE: 61

Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys Ala Lys
            20                  25                  30

<210> SEQ ID NO 62
<211> LENGTH: 32
<212> TYPE: PRT
<213> ORGANISM: artificial sequence
<220> FEATURE:
<223> OTHER INFORMATION: synthetic peptide

<400> SEQUENCE: 62

Arg Phe Thr Ile Ser Leu Asp Thr Ser Lys Ser Thr Ala Tyr Leu Gln
1               5                   10                  15

Met Asn Ser Leu Arg Ala Glu Asp Thr Ala Val Tyr Tyr Cys Ala Lys
            20                  25                  30

<210> SEQ ID NO 63
<211> LENGTH: 11
<212> TYPE: PRT
<213> ORGANISM: artificial sequence
<220> FEATURE:
<223> OTHER INFORMATION: synthetic peptide

<400> SEQUENCE: 63

Trp Gly Leu Gly Thr Glu Val Ile Val Ser Ser
1               5                   10

<210> SEQ ID NO 64
<211> LENGTH: 11
<212> TYPE: PRT
<213> ORGANISM: artificial sequence
<220> FEATURE:
<223> OTHER INFORMATION: synthetic peptide

<400> SEQUENCE: 64

Trp Gly His Gly Thr Glu Val Ile Val Ser Ser
1               5                   10

<210> SEQ ID NO 65
<211> LENGTH: 11
<212> TYPE: PRT
<213> ORGANISM: artificial sequence
<220> FEATURE:
<223> OTHER INFORMATION: synthetic peptide

<400> SEQUENCE: 65

Trp Gly Gln Gly Thr Leu Val Thr Val Ser Ser
1               5                   10

<210> SEQ ID NO 66
<211> LENGTH: 459
<212> TYPE: PRT
<213> ORGANISM: artificial sequence

```
<220> FEATURE:
<223> OTHER INFORMATION: synthetic polypeptide

<400> SEQUENCE: 66

Met Ala Pro Leu Cys Pro Ser Pro Trp Leu Pro Leu Leu Ile Pro Ala
1               5                   10                  15

Pro Ala Pro Gly Leu Thr Val Gln Leu Leu Ser Leu Leu Leu Leu
            20                  25                  30

Val Pro Val His Pro Gln Arg Leu Pro Arg Met Gln Glu Asp Ser Pro
        35                  40                  45

Leu Gly Gly Gly Ser Ser Gly Glu Asp Asp Pro Leu Gly Glu Glu Asp
    50                  55                  60

Leu Pro Ser Glu Glu Asp Ser Pro Arg Glu Glu Asp Pro Pro Gly Glu
65                  70                  75                  80

Glu Asp Leu Pro Gly Glu Glu Asp Leu Pro Gly Glu Glu Asp Leu Pro
                85                  90                  95

Glu Val Lys Pro Lys Ser Glu Glu Gly Ser Leu Lys Leu Glu Asp
            100                 105                 110

Leu Pro Thr Val Glu Ala Pro Gly Asp Pro Gln Glu Pro Gln Asn Asn
        115                 120                 125

Ala His Arg Asp Lys Glu Gly Asp Asp Gln Ser His Trp Arg Tyr Gly
    130                 135                 140

Gly Asp Pro Pro Trp Pro Arg Val Ser Pro Ala Cys Ala Gly Arg Phe
145                 150                 155                 160

Gln Ser Pro Val Asp Ile Arg Pro Gln Leu Ala Ala Phe Cys Pro Ala
                165                 170                 175

Leu Arg Pro Leu Glu Leu Leu Gly Phe Gln Leu Pro Pro Leu Pro Glu
            180                 185                 190

Leu Arg Leu Arg Asn Asn Gly His Ser Val Gln Leu Thr Leu Pro Pro
        195                 200                 205

Gly Leu Glu Met Ala Leu Gly Pro Gly Arg Glu Tyr Arg Ala Leu Gln
    210                 215                 220

Leu His Leu His Trp Gly Ala Ala Gly Arg Pro Gly Ser Glu His Thr
225                 230                 235                 240

Val Glu Gly His Arg Phe Pro Ala Glu Ile His Val Val His Leu Ser
                245                 250                 255

Thr Ala Phe Ala Arg Val Asp Glu Ala Leu Gly Arg Pro Gly Gly Leu
            260                 265                 270

Ala Val Leu Ala Ala Phe Leu Glu Glu Gly Pro Glu Glu Asn Ser Ala
        275                 280                 285

Tyr Glu Gln Leu Leu Ser Arg Leu Glu Glu Ile Ala Glu Glu Gly Ser
    290                 295                 300

Glu Thr Gln Val Pro Gly Leu Asp Ile Ser Ala Leu Leu Pro Ser Asp
305                 310                 315                 320

Phe Ser Arg Tyr Phe Gln Tyr Glu Gly Ser Leu Thr Thr Pro Pro Cys
                325                 330                 335

Ala Gln Gly Val Ile Trp Thr Val Phe Asn Gln Thr Val Met Leu Ser
            340                 345                 350

Ala Lys Gln Leu His Thr Leu Ser Asp Thr Leu Trp Gly Pro Gly Asp
        355                 360                 365

Ser Arg Leu Gln Leu Asn Phe Arg Ala Thr Gln Pro Leu Asn Gly Arg
    370                 375                 380

Val Ile Glu Ala Ser Phe Pro Ala Gly Val Asp Ser Ser Pro Arg Ala
385                 390                 395                 400
```

```
Ala Glu Pro Val Gln Leu Asn Ser Cys Leu Ala Ala Gly Asp Ile Leu
            405                 410                 415

Ala Leu Val Phe Gly Leu Leu Phe Ala Val Thr Ser Val Ala Phe Leu
            420                 425                 430

Val Gln Met Arg Arg Gln His Arg Arg Gly Thr Lys Gly Gly Val Ser
        435                 440                 445

Tyr Arg Pro Ala Glu Val Ala Glu Thr Gly Ala
    450                 455
```

ANTI-CARBONIC ANHYDRASE IX ANTIBODY

RELATED APPLICATION

This application is a U.S. national stage entry of PCT Application No. PCT/US19/30807, filed May 6, 2019. The entire contents of which are incorporated herein by reference for all purposes.

FIELD OF THE INVENTION

The invention generally relates to cancer treatment field. Particularly, the invention relates to antigenic peptides of carbonic anhydrase IX (CAIX), anti-CAIX antibodies and their use in the prevention and/or treatment of cancers.

BACKGROUND OF THE INVENTION

Hypoxia is a salient feature of rapidly growing malignant tumors and their metastases. During the early stage of tumor development, tissue hypoxia occurs due to insufficient blood supply. Hypoxia and acidification of the extratumoral environment are both associated with aggressive tumor growth, metastasis formation and poor response to radiotherapy, surgery and/or to anticancer chemotherapy. Carbonic anhydrases (CAs) are involved in diverse physiological functions including pH regulation, ion transport, bone resorption and secretion of gastric, cerebrospinal fluid and pancreatic juices. CAIX expression in normal tissue is limited to the basolateral surface of gastric, intestinal (proliferating crypt enterocytes of the duodenum, jejunum and ileal mucosa), and gallbladder epithelia in human. CAIX is overexpressed in many solid tumors but not in their corresponding normal tissues. Previous studies report that CAIX expression was up-regulated and associated with poor prognosis in cancers of the lung, breast, liver, cervix, colon, ovaries, bladder, head and neck, brain, and oral cavity.

US 20050158809 relates to methods of aiding in a renal cell carcinoma prognosis that includes quantifying expressed carbonic anhydrase in samples derived from renal cell carcinoma patients. US 20130274305 relates to CAIX inhibitors comprising a nitroimidazole moiety including their use in cancer treatment. US 20130336923 provides scFv antibodies and monoclonal antibodies that bind to and decrease an activity of CAIX.

There is a need in this art for new antibodies against CAIX for use in pharmaceutical applications including cancer therapy.

SUMMARY OF THE INVENTION

The present disclosure provides an antigenic peptide comprising an epitope of CAIX having an amino acid sequence of SEQ ID NO:32 or SEQ ID NO:33 or an amino acid sequence of SEQ ID NO:32 and SEQ ID NO:33. Accordingly, the present disclosure provides an immunogenic composition comprising the antigenic peptide of the present disclosure and optional a pharmaceutically acceptable adjuvant. Also provided is an antibody specifically binds an epitope of the present disclosure.

The present disclosure also provides an isolated anti-CAIX antibody or an antigen-binding portion thereof, comprising at least one of a light chain complementarity determining region 1 (L-CDR1) of SEQ ID NO:1, 4 or 6 or a variant thereof, a light chain CDR2 (L-CDR2) of SEQ ID NO:2, 5 or 7 or a variant thereof, and a light chain CDR3 (L-CDR3) of SEQ ID NO:3 or 8 or a variant thereof, and at least one of a heavy chain CDR1 (H-CDR1) of SEQ ID NO:9, 12, 15 or 18 or a variant thereof, a heavy chain CDR2 (H-CDR2) of SEQ ID NO: 10, 13, 16 or 19 or a variant thereof, and a heavy chain CDR3 (H-CDR3) of SEQ ID NO: 11, 14, 17 or 20 or a variant thereof, such that said isolated antibody or antigen-binding portion thereof binds to CAIX.

The related embodiments of the isolated anti-CAIX antibody include a constant region and one or more heavy and light chain variable framework regions of a human antibody sequence. In a related embodiment, the isolated anti-CAIX antibody comprises framework regions with at least 70% identity to Avastin.

The related embodiments include an isolated antibody that specifically binds CAIX as disclosed herein includes up to 10 amino acid substitutions (such as up to 1, 2, 3, 4, 5, 6, 7, 8, or up to 9 amino acid substitutions) in the framework regions.

The related embodiments of the framework regions include L-FR1 having an amino acid sequence selected from of SEQ ID NOs: 34 to 37, L-FR2 having an amino acid sequence selected from of SEQ ID NOs:38 to 40, L-FR3 having an amino acid sequence selected from of SEQ ID NOs:41 to 43 and L-FR4 having an amino acid sequence selected from of SEQ ID NOs: 44 to 45 and H-FR1 having an amino acid sequence selected from of SEQ ID NOs:46 to 52, H-FR2 having an amino acid sequence selected from of SEQ ID NOs:53 to 56, H-FR3 having an amino acid sequence selected from of SEQ ID NOs:57 to 62 and H-FR4 having an amino acid sequence selected from of SEQ ID NOs:63 to 65.

The present disclosure also provides a light chain comprising an amino acid sequence having a sequence selected from the group consisting of as set forth in SEQ ID NOs: 21 to 23.

The present disclosure also provides a heavy chain comprising an amino acid sequence having a sequence selected from the group consisting of as set forth in SEQ ID NOs: 24 to 28.

The present disclosure further provides an isolated antibody or an antigen-binding portion thereof, comprising (i) a light chain having an amino acid sequence as set forth in the sequence selected from the group consisting of SEQ ID NOs: 21 to 23 or a variant thereof, and (ii) a heavy chain having an amino acid sequence as set forth in the sequence selected from the group consisting of SEQ ID NOs: 24 to 28 or a variant thereof. In one embodiment, the variant has at least 80% sequence identity to the corresponding sequence. Certain embodiments of the isolated antibody include a light chain having an amino acid sequence as set forth in SEQ ID NO: 21 and a heavy chain having an amino acid sequence as set forth in SEQ ID NO: 24; a light chain having an amino acid sequence as set forth in SEQ ID NO: 22 and a heavy chain having an amino acid sequence as set forth in SEQ ID NO: 25; a light chain having an amino acid sequence as set forth in SEQ ID NO: 21 and a heavy chain having an amino acid sequence as set forth in SEQ ID NO: 26; a light chain having an amino acid sequence as set forth in SEQ ID NO: 23 and a heavy chain having an amino acid sequence as set forth in SEQ ID NO: 27; or a light chain having an amino acid sequence as set forth in SEQ ID NO: 21 and a heavy chain having an amino acid sequence as set forth in SEQ ID NO: 28.

Certain embodiments relate to cells expressing an antibody of the present disclosure or an antigen-binding portion thereof.

Certain embodiments relate to a pharmaceutical composition comprising an antibody against CAIX of the present disclosure or a cell expressing an antibody of the present disclosure or an antigen-binding portion thereof and a pharmaceutically acceptable carrier or excipient.

Certain embodiments are directed to a method for preventing and/or treating a cancer in a subject, comprising in vitro expressing an antibody of the present disclosure or an antigen-binding portion thereof in a cell and administering the cell to the subject.

DETAILED DESCRIPTION OF THE INVENTION

Figure 1:
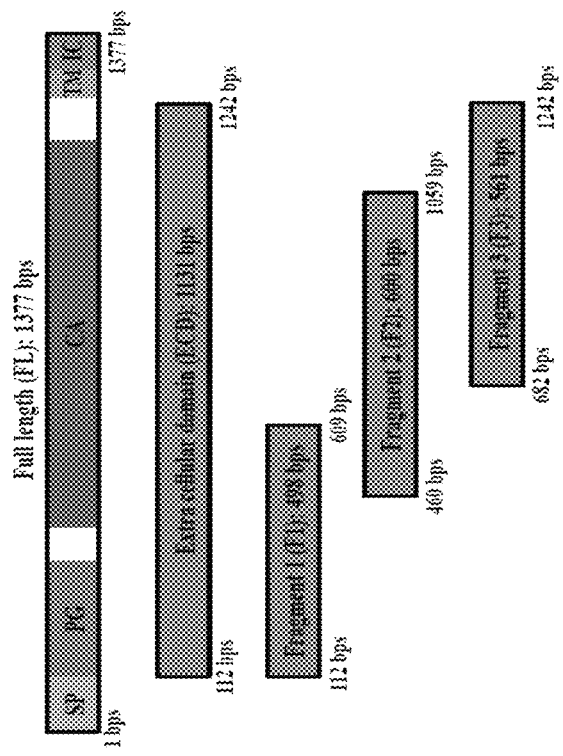
FIGS. 1 (A) to (C) show purification of (A), anti-CAIX scFv (NAVICA9S1, NAVICA9S2, NAVICA9L1, NAVICA9L2, NAVICA9L3) and (B), CAIX protein (ECD, F3) and (C), the size of the the full length, extra-cellular domain (ECD), fragment 1 (F1), fragment 2 (F2) and fragment 3 (F3) of CAIX. Lane 1: supernatant after $Ni^{2+}$ sepharose binding; Lane 2: collection of washing buffer; Lane 3: $Ni^{2+}$ sepharose after elution; Lane 4: collection of eluted proteins; ECD: extracellular domain; and F3: fragment 3.

The present disclosure is based on the discovery of epitopes located in CAIX and anti-CAIX antibodies having binding activity with cancer cells.

In the description that follows, a number of terms are used and the following definitions are provided to facilitate understanding of the claimed subject matter. Terms that are not expressly defined herein are used in accordance with their plain and ordinary meanings.

Unless otherwise specified, "a" or "an" means "one or more."

As used herein, the term "epitope" refers to the site on the antigen to which an antibody binds.

As used herein, the term "specifically binds" means that an antibody does not cross react to a significant extent with other epitopes.

As used herein, the term "antibody" refers to single chain, two-chain, and multi-chain proteins and polypeptides belonging to the classes of polyclonal, monoclonal, chimeric, and humanized antibodies; it also includes synthetic and genetically engineered variants of these antibodies. "Antibody fragment" includes Fab, Fab', F(ab')$_2$, and Fv fragments, as well as any portion of an antibody having specificity toward a desired target epitope or epitopes.

As used herein, the term "monoclonal antibody" refers to an antibody obtained from a population of substantially homogeneous antibodies. In other words, a monoclonal antibody consists of a homogeneous antibody arising from the growth of a single cell clone (for example a hybridoma, a eukaryotic host cell transfected with a DNA molecule coding for the homogeneous antibody or a prokaryotic host cell transfected with a DNA molecule coding for the homogeneous antibody). These antibodies are directed against a single epitope and are therefore highly specific.

As used herein, the term "complementarity determining region" (CDR) refers to the non-contiguous antigen combining sites found within the variable region of both heavy and light chain polypeptides. CDRs have been described by Kabat et al., J. Biol. Chem. 252:6609-6616 (1977); Kabat et al., U.S. Dept. of Health and Human Services, "Sequences of proteins of immunological interest" (1991); by Chothia et al., J. Mol. Biol. 196:901-917 (1987); and MacCallum et al., J. Mol. Biol. 262:732-745 (1996), where the definitions include overlapping or subsets of amino acid residues when compared against each other.

As used herein, the term "framework" or FR residues are those variable domain residues other than the hypervariable region residues.

As used herein, the term "humanized antibody" refers to a recombinant protein in which the CDRs from an antibody from one species; e.g., a murine or a chicken antibody, are transferred from the heavy and light variable chains of the antibody from the species into human heavy and light variable domains (framework regions). The constant domains of the antibody molecule are derived from those of a human antibody. In some cases, specific residues of the framework region of the humanized antibody, particularly those that are touching or close to the CDR sequences, may be modified, for example replaced with the corresponding residues from the original murine, rodent, subhuman primate, or other antibody. The humanized antibody may be achieved by various methods including (a) grafting only the non-human CDRs onto human framework and constant regions with or without retention of critical framework residues, or (b) transplanting the entire non-human variable domains, but "cloaking" them with a human-like section by replacement of surface residues. Such methods as are useful in practicing the present disclosure include that disclosed in Padlan, Mol. Immunol., 31(3):169-217 (1994).

As used herein, the term "chimeric antibody" refers to a recombinant protein that contains the variable domains of both the heavy and light antibody chains, including the complementarity determining regions (CDRs) of an antibody derived from one species, preferably a rodent antibody or a chicken antibody, more preferably a murine antibody, while the constant domains of the antibody molecule are derived from those of a human antibody.

As used herein, the term "antigen-binding" refers to the ability to specifically bind to an antigen. It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a single domain or dAb (domain antibody) fragment, which consists of a VH domain; and (vi) an isolated complementarity determining region (CDR) or (vii) a combination of two or more isolated CDRs which may optionally be joined by a synthetic linker. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv)). These antibody fragments are obtained using conventional techniques known to those with skill in the art, and the fragments are screened for utility in the same manner as are intact antibodies.

As used herein, a single chain antibody ("SCA") comprises single chain Fv fragments ("scFv") in which the variable light ("VL") and variable heavy ("VH") domains are linked by a peptide bridge or by disulfide bonds.

As used herein, the term "linker" refers to a bi-functional molecule that can be used to link two molecules into one contiguous molecule. In some cases, a linker is a peptide within an antibody-binding fragment (such as an Fv fragment), which serves to indirectly bond the variable heavy chain to the variable light chain.

As used herein, the term $K_D$ refers to the dissociation constant for a given interaction, such as a polypeptide ligand interaction or an antibody antigen interaction. For example, for the bimolecular interaction of an antibody (such as one disclosed herein) and an antigen, it is the concentration of the individual components of the bimolecular interaction divided by the concentration of the complex.

As used herein, the terms "treatment," "treating," and the like, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

As interchangeably used herein, the terms "individual," "subject," "host," and "patient," refer to a mammal, including, but not limited to, murines (rats, mice), non-human primates, humans, canines, felines, ungulates (e.g., equines, bovines, ovines, porcines, caprines), etc.

As used herein, the term "therapeutically effective amount" or "efficacious amount" refers to the amount of a subject anti-CAIX antibody that, when administered to a mammal or other subject for treating a disease, is sufficient to effect such treatment for the disease.

In one aspect, the present disclosure provides an antigenic peptide comprising an epitope of CAIX having an amino acid sequence:

(SEQ ID NO: 32)
QRLPRIVIQEDSPLGGGSSGEDDPLGEEDLPSEEDSPREEDPPGEEDLP
GEEDLPGEEDLPEVKPKSEEEGSLKLEDLPTVEAPGDPQEPQNNAHRDK
EGDDQSHWRYGGDPPWPRVS;
or (SEQ ID NO: 33)
HWGAAGRPGSEHTVEGHRFPAEIHVVHLSTAFARVDEALGRPGGLAVLA
AFLEEGPEENSAYEQLLSRLEEIAEEGSETQVPGLDISALLPSDFSRYF
QYEGSLTTPPCAQGVIWTVFNQTVMLSA;
or an amino acid sequence of SEQ ID NO:32 and SEQ ID NO:33.

Accordingly, the present disclosure provides an immunogenic composition comprising the antigenic peptide of the present disclosure and optional a pharmaceutically acceptable adjuvant. Examples of pharmaceutically acceptable adjuvants may include aluminum hydroxide, alum, Alhydrogel (aluminum trihydrate) or other aluminum-comprising salts, virosomes, nucleic acids comprising CpG motifs, squalene, oils, MF59, QS21, various saponins, virus-like particles, monophosphoryl-lipidA/trehalose dicorynomycolate, toll-like receptor agonists, copolymers such as polyoxypropylene and polyoxyethylene, or the like.

The present disclosure also provides an antibody specifically binds an epitope of the present disclosure. Antibodies capable of binding to the novel epitope are useful as diagnostics, therapeutic agents, and vaccines.

In one embodiment, the present disclosure provides an isolated anti-CAIX antibody or an antigen-binding portion thereof, comprising at least one of a light chain complementarity determining region 1 (L-CDR1) of SEQ ID NO:1, 4 or 6 or a variant thereof, a light chain CDR2 (L-CDR2) of SEQ ID NO:2, 5 or 7 or a variant thereof, and a light chain CDR3 (L-CDR3) of SEQ ID NO:3 or 8 or a variant thereof, and at least one of a heavy chain CDR1 (H-CDR1) of SEQ ID NO:9, 12, 15 or 18 or a variant thereof, a heavy chain CDR2 (H-CDR2) of SEQ ID NO: 10, 13, 16 or 19 or a variant thereof, and a heavy chain CDR3 (H-CDR3) of SEQ ID NO: 11, 14, 17 or 20 or a variant thereof, such that said isolated antibody or antigen-binding portion thereof binds to CAIX.

In one embodiment, the variant has an amino acid sequence with at least 80% sequence identity to its corresponding CDR. Preferably, the sequence identity as mentioned above is at least 81%, 82%, 83%, 84%, 85%, 86%, 87%, 88%, 89%, 90%, 91%, 91%, 92%, 93%, 94%, 95%, 96%, 97%, 98% or 99%.

The amino acid sequences of the complementarity determining regions in heavy chains and light chains are listed in below table.

| CDRs of Light Chain | | |
| --- | --- | --- |
| L-CDR1 | L-CDR2 | L-CDR3 |
| SGSSGSYG (SEQ ID NO: 1) | YNDKRPS (SEQ ID NO: 2) | GSADRSGAGI (SEQ ID NO: 3) |
| SGSRGSYG (SEQ ID NO: 4) | YNVKRPS (SEQ ID NO: 5) | |
| SGGGKNYG (SEQ ID NO: 6) | LNDKRPS (SEQ ID NO: 7) | GSRDSSPT (SEQ ID NO: 8) |

| CDRs of Heavy Chain | | |
| --- | --- | --- |
| H-CDR1 | H-CDR2 | H-CDR3 |
| SHGMA (SEQ ID NO: 9) | GISNTGRYTNYGSAVKG (SEQ ID NO: 10) | AAVNCVYGCPGSIDA (SEQ ID NO: 11) |

-continued

| CDRs of Heavy Chain | | |
|---|---|---|
| H-CDR1 | H-CDR2 | H-CDR3 |
| SYAIQ (SEQ ID NO: 12) | GISDDGSWTGYGAAVKG (SEQ ID NO: 13) | GAGTGYCANRSFGCASTIDA (SEQ ID NO: 14) |
| SFNMF (SEQ ID NO: 15) | AISSDGSRSRYGSAVQG (SEQ ID NO: 16) | RPYSGCTSNNFCFNAAYIDV (SEQ ID NO: 17) |
| SYAMN (SEQ ID NO: 18) | GITNTGSSAGYGAAVKG (SEQ ID NO: 19) | SYGGWCDHACAPDDIDT (SEQ ID NO: 20) |

In some embodiments, the isolated anti-CAIX antibody is a monoclonal antibody, chimeric antibody, humanized antibody or human antibody.

Each heavy and light chain contains a constant region and a variable region, (the regions are also known as "domains"). In several embodiments, the heavy and the light chain variable domains combine to specifically bind the antigen. Light and heavy chain variable domains contain a "framework" region interrupted by three hypervariable regions, also called "complementarity-determining regions" or "CDRs" (see, e.g., Kabat et al., Sequences of Proteins of Immunological Interest, U.S. Department of Health and Human Services, 1991). The sequences of the framework regions of different light or heavy chains are relatively conserved within a species. The framework region of an antibody, that is the combined framework regions of the constituent light and heavy chains, serves to position and align the CDRs in three-dimensional space. The CDRs are primarily responsible for binding to an epitope of an antigen. The amino acid sequence boundaries of a given CDR can be readily determined using any of a number of well-known schemes, including those described by Kabat et al. ("Sequences of Proteins of Immunological Interest," 5th Ed. Public Health Service, National Institutes of Health, Bethesda, Md., 1991; "Kabat" numbering scheme), Al-Lazikani et al., (JMB 273,927-948, 1997; "Chothia" numbering scheme), and Lefranc, et al. ("IMGT unique numbering for immunoglobulin and T cell receptor variable domains and Ig superfamily V-like domains," Dev. Comp. Immunol., 27:55-77, 2003; "IMGT" numbering scheme).

In some embodiments, the isolated anti-CAIX antibody comprises a constant region and one or more heavy and light chain variable framework regions of a human antibody sequence. In a related embodiment, the antibody comprises a modified or unmodified constant region of a human IgG1, IgG2, IgG3 or IgG4. In a preferred embodiment, the constant region is human IgG1 or IgG4, which may optionally be modified to enhance or decrease certain properties. In a related embodiment, the isolated anti-CAIX antibody comprises framework regions with at least 70% identity to Avastin.

In some embodiments, an isolated antibody that specifically binds CAIX as disclosed herein includes up to 10 amino acid substitutions (such as up to 1, 2, 3, 4, 5, 6, 7, 8, or up to 9 amino acid substitutions) in the framework regions (for example, according to the Kabat, Clothia or IMGT numbering systems) of the heavy chain of the antibody, the light chain of the antibody, or the heavy and light chains of the antibody. In some embodiments, the framework regions comprises L-FR1 having an amino acid sequence selected from of SEQ ID NOs: 34 to 37, L-FR2 having an amino acid sequence selected from of SEQ ID NOs:38 to 40, L-FR3 having an amino acid sequence selected from of SEQ ID NOs:41 to 43 and L-FR4 having an amino acid sequence selected from of SEQ ID NOs: 44 to 45 and H-FR1 having an amino acid sequence selected from of SEQ ID NOs:46 to 52, H-FR2 having an amino acid sequence selected from of SEQ ID NOs:53 to 56, H-FR3 having an amino acid sequence selected from of SEQ ID NOs:57 to 62 and H-FR4 having an amino acid sequence selected from of SEQ ID NOs:63 to 65.

```
Light chain
L-FR1
                                          (SEQ ID NO: 34)
ALTQPSSVSANLGETVEITC (SEQ ID NO: 35)
ALTQPSSVSANPGETVKITC (SEQ ID NO: 36)
AIQMTQSPSSLSASVGDRVTITCRAS (SEQ ID NO: 37)
DIQMTQSPSSLSASVGDRVTITCSAS

L-FR2
                                          (SEQ ID NO: 38)
WYQQKSPGSAPVTVIY (SEQ ID NO: 39)
VAWYQQKPGKAPKLLIY (SEQ ID NO: 40)
LNWYQQKPGKAPKVLIY

L-FR3
                                          (SEQ ID NO: 41)
DIPSRFSGSKSGSTGTLTITGVQAEDEAVYYC (SEQ ID NO: 42)
NIPSRFSGSKSGSTHTLTITGVQAEDEAVYFC (SEQ ID NO: 43)
GVPSRFSGSGSGTDFTLTISSLQPEDFATYYC

L-FR4
                                          (SEQ ID NO: 44)
FGAGTTLTVL (SEQ ID NO: 45)
FGQGTKVEIK

Heavy chain
H-FR1
                                          (SEQ ID NO: 46)
AVTLDEPGGGLQTPGGTLSLVCKASGFDS (SEQ ID NO: 47)
AVTLDESGGGLQTPGGSLSLVCKASGFTFS (SEQ ID NO: 48)
AVTLDESGGGLQTPGGALSLVCKASGFTFS
```

```
                                              (SEQ ID NO: 49)
AVTLDESEGGLQTPGGALSLVCKASGFTFS (SEQ ID NO: 50)
AVTLDESGGGLQTPRGALSLVCKASGFTFS (SEQ ID NO: 51)
EVQLVESGGGLVQPGGSLRLSCAASGFTFI (SEQ ID NO: 52)
EVQLVESGGGLVQPGGSLRLSCAASGYTFT

H-FR2
                                              (SEQ ID NO: 53)
WVRQAPGKGLEYVA (SEQ ID NO: 54)
WVRQAPGKGLEWVA (SEQ ID NO: 55)
WVRQAPGKGLEFVA (SEQ ID NO: 56)
WVRQAPGKGLEWVG

H-FR3
                                              (SEQ ID NO: 57)
RATISRDNGQSTVRLQLNDLRAEDAGTYFCAR (SEQ ID NO: 58)
RATISRDNGQSTMRLQLNNLRAEDTGIYYCAK (SEQ ID NO: 59)
RATISRDNGQSTVRLQLNSLRAEDTGTYYCAK (SEQ ID NO: 60)
RATISRDNGQSTVRLQLNNLRAEDTATYFCTK (SEQ ID NO: 61)
RFTISADTSKNTAYLQMNSLRAEDTAVYYCAK (SEQ ID NO: 62)
RFTISLDTSKSTAYLQMNSLRAEDTAVYYCAK

H-FR4
                                              (SEQ ID NO: 63)
WGLGTEVIVSS (SEQ ID NO: 64)
WGHGTEVIVSS (SEQ ID NO: 65)
WGQGTLVTVSS
```

According to the present disclosure, the embodiments of the amino acids of the light chains and heavy chains of the antibodies of the present disclosure are listed below.

Embodiments of Amino Acid Sequences of Light chains

```
ALTQPSSVSANLGETVEITCSGSSGSYGWYQQKSPGSAPVTVIYYNDKR
PSDIPSRFSGSKSGSTGTLTITGVQAEDEAVYYCGSADRSGAGIFGAGT
TLTVL (SEQ ID NO: 21) (NAVICA9L1)

ALTQPSSVSANLGETVEITCSGSRGSYGWYQQKSPGSAPVTVIYYNVKR
PSDIPSRFSGSKSGSTGTLTITGVQAEDEAVYYCGSADRSGAGIFGAGT
TLTVL (SEQ ID NO: 22) (NAVICA9L2)

ALTQPSSVSANLGETVEITCSGSSGSYGWYQQKSPGSAPVTVIYYNDKR
PSDIPSRFSGSKSGSTGTLTITGVQAEDEAVYYCGSADRSGAGIFGAGT
TLTVL (SEQ ID NO: 21) (NAVICA9L3)

ALTQPSSVSANPGETVKITCSGGGKNYGWYQQKSPGSAPVTVIYLNDKR
PSNIPSRFSGSKSGSTHTLTITGVQAEDEAVYFCGSRDSSPTFGAGTTL
TVL (SEQ ID NO: 23) (NAVICA9S1)

ALTQPSSVSANLGETVEITCSGSSGSYGWYQQKSPGSAPVTVIYYNDKR
PSDIPSRFSGSKSGSTGTLTITGVQAEDEAVYYCGSADRSGAGIFGAGT
TLTVL (SEQ ID NO: 21) (NAVICA9S2)
```

Embodiments of Amino Acid Sequences of Heavy chains

```
AVTLDEPGGGLQTPGGTLSLVCKASGFDISSHGMAWVRQAPGKGLEYVA
GISNTGRYTNYGSAVKGRATISRDNGQSTVRLQLNDLRAEDAGTYFCAR
AAVNCVYGCPGSIDAWGLGTEVIVSS (SEQ ID NO: 24)
(NAVICA9L1)

AVTLDESGGGLQTPGGGLSLVCKASGFTFSSYAIQWVRQAPGKGLEWVA
GISDDGSWTGYGAAVKGRATISRDNGQSTMRLQLNNLRAEDTGIYYCAK
GAGTGYCANRSFGCASTIDAWGHGTEVIVSS (SEQ ID NO: 25)
(NAVICA9L2)

AVTLDESGGGLQTPGGALSLVCKASGFTFSSFNMFWVRQAPGKGLEYVA
AISSDGSRSRYGSAVQGRATISRDNGQSTVRLQLNSLRAEDTGTYYCAK
RPYSGCTSNNFCFNAAYIDVWGHGTEVIVSS (SEQ ID NO: 26)
(NAVICA9L3)

AVTLDESEGGLQTPGGALSLVCKASGFTFSSYAMNWVRQAPGKGLEFVA
GITNTGSSAGYGAAVKGRATISRDNGQSTVRLQLNNLRAEDTATYFCTK
SYGGWCDHACAPDDIDTWGHGTEVIVSS (SEQ ID NO: 27)
(NAVICA9S1)

AVTLDESGGGLQTPRGALSLVCKASGFTFSSFNMFWVRQAPGKGLEYVA
AISSDGSRSRYGSAVQGRATISRDNGQSTVRLQLNSLRAEDTGTYYCAK
RPYSGCTSNNFCFNAAYIDVWGHGTEVIVSS (SEQ ID NO: 28)
(NAVICA9S2)
```

In some embodiments, the present disclosure provides a light chain comprising an amino acid sequence having a sequence selected from the group consisting of as set forth in SEQ ID NOs: 21 to 23.

In some embodiments, the present disclosure provides a heavy chain comprising an amino acid sequence having a sequence selected from the group consisting of as set forth in SEQ ID NOs: 24 to 28.

In further embodiments, the present disclosure comprises an isolated antibody or an antigen-binding portion thereof, comprising (i) a light chain having an amino acid sequence as set forth in the sequence selected from the group consisting of SEQ ID NOs: 21 to 23 or a variant thereof, and (ii) a heavy chain having an amino acid sequence as set forth in the sequence selected from the group consisting of SEQ ID NOs: 24 to 28 or a variant thereof. In one embodiment, the variant has at least 80% sequence identity to the corresponding sequence. In one embodiment, the variant has at least 80% sequence identity to the framework of the light chain or the heavy chain. Preferably, the sequence identity as mentioned above is at least 90%, 91%, 91%, 92%, 93%, 94%, 95%, 96%, 97%, 98% or 99%.

In a further embodiment, the present disclosure comprises an isolated antibody or an antigen-binding portion thereof, comprising a light chain having an amino acid sequence as set forth in SEQ ID NO: 21 and a heavy chain having an amino acid sequence as set forth in SEQ ID NO: 24; a light chain having an amino acid sequence as set forth in SEQ ID NO: 22 and a heavy chain having an amino acid sequence as set forth in SEQ ID NO: 25; a light chain having an amino acid sequence as set forth in SEQ ID NO: 21 and a heavy chain having an amino acid sequence as set forth in SEQ ID NO: 26; a light chain having an amino acid sequence as set forth in SEQ ID NO: 23 and a heavy chain having an amino acid sequence as set forth in SEQ ID NO: 27; or a light chain having an amino acid sequence as set forth in SEQ ID NO: 21 and a heavy chain having an amino acid sequence as set forth in SEQ ID NO: 28.

In a further embodiment, the present disclosure provides a single chain variable fragment (scFv) that binds CAIX, comprising a) a light chain variable region of the light chain having an amino acid sequence as set forth in the sequence selected from the group consisting of SEQ ID NOs: 21 to 23; b) a linker; and c) a heavy chain variable region of the heavy chain having an amino acid sequence as set forth in the sequence selected from the group consisting of SEQ ID NOs: 24 to 28. In one embodiment, the linker is a peptide linker. In some embodiments, the linker comprises 4-20 amino acids. In some embodiments, the linker comprises a peptide having an amino acid sequence of GQSSRSS (SEQ ID NO:29), GQSSRSSSGGGSSGGGGS (SEQ ID NO:30) or GQSSRSSGGGGSSGGGS (SEQ ID NO:31).

Techniques for preparing monoclonal antibodies against virtually any target antigen are well known in the art. See, for example, Kohler and Milstein, Nature 256: 495 (1975), and Coligan et al. (eds.), CURRENT PROTOCOLS IN IMMUNOLOGY, VOL. 1, pages 2.5.1-2.6.7 (John Wiley & Sons 1991). Briefly, monoclonal antibodies can be obtained by injecting mice or chicken with a composition comprising an antigen, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures. In another example, phage display techniques for preparing an antibody are also known in the art. Phage display of antibody libraries has become a powerful method for both studying the immune response as well as a method to rapidly select and evolve desired antibodies. This technology relies on the utilization of phage display libraries in a screening process known as biopanning (George K. et al., Affinity Chromatography pp 195-208).

Various techniques, such as production of chimeric or humanized antibodies, may involve procedures of antibody cloning and construction. The antigen-binding variable light chain and variable heavy chain sequences for an antibody of interest may be obtained by a variety of molecular cloning procedures, such as RT-PCR, 5'-RACE, and cDNA library screening. The variable heavy or light chain sequence genes of an antibody from a cell that expresses a murine antibody can be cloned by PCR amplification and sequenced. To confirm their authenticity, the cloned $V_L$ and $V_H$ genes can be expressed in cell culture as a chimeric antibody as described by Orlandi et al., (Proc. Natl. Acad. Sci., USA, 86: 3833 (1989)). Based on the variable heavy or light chain gene sequences, a humanized antibody can then be designed and constructed as described by Leung et al. (Mol. Immunol., 32: 1413 (1995)).

A chimeric antibody is a recombinant protein in which the variable regions of a human antibody have been replaced by the variable regions of, for example, a mouse antibody, including the complementarity-determining regions (CDRs) of the mouse antibody. Chimeric antibodies exhibit decreased immunogenicity and increased stability when administered to a subject. Methods for constructing chimeric antibodies are well known in the art (e.g., Leung et al., 1994, Hybridoma 13:469).

A chimeric monoclonal antibody may be humanized by transferring the mouse CDRs from the heavy and light variable chains of the mouse immunoglobulin into the corresponding variable domains of a human antibody. The mouse framework regions (FR) in the chimeric monoclonal antibody are also replaced with human FR sequences. To preserve the stability and antigen specificity of the humanized monoclonal, one or more human FR residues may be replaced by the mouse counterpart residues. Humanized monoclonal antibodies may be used for therapeutic treatment of subjects. Techniques for production of humanized monoclonal antibodies are well known in the art. (See, e.g., Jones et al., 1986, Nature, 321:522; Riechmann et al., Nature, 1988, 332:323; Verhoeyen et al., 1988, Science, 239:1534; Carter et al., 1992, Proc. Nat'l Acad. Sci. USA, 89:4285; Sandhu, Crit. Rev. Biotech., 1992, 12:437; Tempest et al., 1991, Biotechnology 9:266; Singer et al., J. Immun., 1993, 150:2844.

Modifications can be made to a nucleic acid encoding a polypeptide described herein without diminishing its biological activity. Some modifications can be made to facilitate the cloning, expression, or incorporation of the targeting molecule into a fusion protein. Such modifications are well known to those of skill in the art and include, for example, termination codons, a methionine added at the amino terminus to provide an initiation, site, additional amino acids placed on either terminus to create conveniently located restriction sites, or additional amino acids (such as poly His) to aid in purification steps. In addition to recombinant methods, the antibodies of the present disclosure can also be constructed in whole or in part using standard peptide synthesis well known in the art.

As a modification to the two chain antibody purification protocol, the heavy and light chain regions are separately solubilized and reduced and then combined in the refolding solution. An exemplary yield is obtained when these two proteins are mixed in a molar ratio such that a 5 fold molar excess of one protein over the other is not exceeded. Excess oxidized glutathione or other oxidizing low molecular weight compounds can be added to the refolding solution after the redox-shuffling is completed.

In addition to recombinant methods, the antibodies and variants thereof that are disclosed herein can also be constructed in whole or in part using standard peptide synthesis. Solid phase synthesis of the polypeptides can be accomplished by attaching the C-terminal amino acid of the sequence to an insoluble support followed by sequential addition of the remaining amino acids in the sequence. Techniques for solid phase synthesis are described by Barany & Merrifield, The Peptides: Analysis, Synthesis, Biology. Vol. 2: Special Methods in Peptide Synthesis, Part A. pp. 3-284; Merrifield et al., J. Am. Chem. Soc. 85:2149-2156, 1963, and Stewart et al., Solid Phase Peptide Synthesis, 2nd ed., Pierce Chem. Co., Rockford, Ill., 1984. Proteins of greater length may be synthesized by condensation of the amino and carboxyl termini of shorter fragments.

Antibody Compositions, Cells Expressing the Antibody and Methods of Administrations Certain embodiments relate to cells expressing an antibody of the present disclosure or an antigen-binding portion thereof. The cells can be produced by culturing a polynucleotide encoding an antibody or an antigen-binding portion thereof in a medium for expressing the antibody of the present disclosure or an antigen-binding portion thereof and harvesting the antibody of the present disclosure or an antigen-binding portion thereof from the medium. Alternatively, the cells can be produced by transfected with a viral vector that expresses an antibody.

Certain embodiments relate to a pharmaceutical composition comprising an antibody against CAIX of the present disclosure or a cell expressing an antibody of the present disclosure or an antigen-binding portion thereof and a pharmaceutically acceptable carrier or excipient. By "pharmaceutically acceptable carrier" is intended, but not limited to, a non-toxic solid, semisolid or liquid filler, diluent, encapsulating material or formulation auxiliary of any type known to persons skilled in the art. Diluents, such as polyols, polyethylene glycol and dextrans, may be used to increase the biological half-life of the conjugate.

The pharmaceutical compositions of the present disclosure can be formulated according to conventional methods (for example, Remington's Pharmaceutical Science, latest edition, Mark Publishing Company, Easton, U.S.A.), and may also contain pharmaceutically acceptable carriers and additives. Examples include, but are not limited to, surfactants, excipients, coloring agents, flavoring agents, preservatives, stabilizers, buffers, suspension agents, isotonic agents, binders, disintegrants, lubricants, fluidity promoting agents, and corrigents, and other commonly used carriers can be suitably used. Specific examples of the carriers include light anhydrous silicic acid, lactose, crystalline cellulose, mannitol, starch, carmellose calcium, carmellose sodium, hydroxypropyl cellulose, hydroxypropyl methylcellulose, polyvinylacetal diethylaminoacetate, polyvinylpyrrolidone, gelatin, medium-chain triglyceride, polyoxyethylene hardened castor oil 60, saccharose, carboxymethyl cellulose, corn starch, inorganic salt, and such.

Certain embodiments are directed to a method for preventing and/or treating a cancer in a subject comprising administering an anti-CAIX antibody of the present disclosure or a cell expressing an antibody of the present disclosure or an antigen-binding portion thereof to the subject. The present method also comprises administering the anti-CAIX antibody of the present disclosure or a cell expressing an antibody of the present disclosure or an antigen-binding portion thereof concomitantly with, or subsequent to other standard therapies.

Certain embodiments are directed to a method for preventing and/or treating a cancer in a subject, comprising in vitro expressing an antibody of the present disclosure or an antigen-binding portion thereof in a cell and administering the cell to the subject.

In preferred embodiments, the subject is a mammal. Exemplary mammals include human, pig, sheep, goat, horse, mouse, dog, cat, cow, etc. Cancers that may be treated with the antibody or a pharmaceutical composition thereof include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, melanoma, multiple myeloma and B-cell lymphoma, brain, as well as head and neck cancer, and associated metastases. In some embodiments, the cancer is lung cancer or lung adenocarcinoma.

The anti-CAIX antibody or the cells as disclosed herein or the pharmaceutical composition thereof may be administered intravenously, topically, intra-peritoneally, intra-arterially, intra-thecally, intra-vesically, or intratumorally. One of ordinary skill will appreciate that effective amounts of the antibody against cancer or its composition can be determined empirically. It will be understood that, when administered to a human patient, the total daily usage of the anti-CAIX antibody or its composition will be decided by the attending physician within the scope of sound medical judgment. The specific therapeutically effective dose level for any particular patient will depend upon a variety of factors: the type and degree of the cellular response to be achieved; activity of the specific the anti-CAIX antibody or its composition employed; the age, body weight, general health, sex and diet of the patient; the time of administration, route of administration, and rate of excretion of the anti-CAIX antibody or its composition; the duration of the treatment; drugs used in combination or coincidental with the anti-CAIX antibody or its composition; and like factors well known in the medical arts.

Each of the above identified compositions and methods of treatment may additionally include an additional anti-cancer drug and the administration of an additional one or more anti-cancer drug. In the method of treatment, the anti-CAIX antibody of the present disclosure or the cells of the present disclosure can be administered concurrently, subsequently or separately with the additional one or more anti-cancer drug.

The following examples are provided to illustrate certain aspects of the present disclosure and should not be construed to limit the present disclosure in any way.

EXAMPLE

Materials and Methods

Expression and Purification of Recombinant CAIX Proteins

Briefly, CAIX genes were constructed in pET-21a(+) and pET-32a(+) plasmids and the resulting vectors were transformed into *E. coli* BL21 cells. The bacterial culture from single colony was grown in 5 ml LB medium containing ampicillin (50 g/ml) at 37° C. overnight, diluted 100-fold in the same LB medium and further grown until the $OD_{600}$ reached between 0.4 and 0.8. To induce the CAIX protein expression, isopropyl-β-D-thiogalactopyranoside (IPTG) was added to a final concentration of 0.5 mM in the culture. The cell pellet was resuspended in His-binding buffer and lysed by sonication. After centrifugation, the resulting cellular lysate was incubated with a $Ni^{2+}$-sepharose to purify the recombinant CAIX fusion protein according to the manufacturer's instruction (GE Healthcare, IL, USA).

Animal Immunization

Female white leghorn (*Gallus domesticus*) chickens were immunized with 60 g of purified his-CAIX in 0.5 ml Freund's complete adjuvant (Sigma, USA) by an intramuscular injection. Five additional immunizations with his-CAIX in Freund's incomplete adjuvant were performed at intervals of 7 days. After each immunization, polyclonal IgY antibodies in egg yolk were partially purified and titrated by an enzyme-linked immunosorbent assay (ELISA) to determine the presence of humoral anti-CAIX immune response. The IgY antibodies were purified from the yolk using 10% Dextran sulphate. The purified IgY antibodies were dissolved in 5 ml of TBS containing 0.05% sodium azide and stored at −20° C.

Construction of scFv Antibody Libraries and Panning

The antibody libraries were established based on reported techniques and methods (Lee et. al., Appl Environ Microbiol., 82(23): 6973-6982, 2016). Briefly, spleens harvested from chickens following the final immunization were placed immediately in Trizol (Invitrogen, CA, USA) for homogenization. Twenty g of total RNA was reversely transcribed into the first-strand cDNA using a SuperScript RT kit (Invitrogen, USA). After amplification using chicken-specific primers, PCR products of heavy and light chain variable (VH and VL) regions were subjected to a second round of PCR to form full-length scFv fragments with a short linker (such as SEQ ID NO. 29) or long linker (SEQ ID NO: 30 or 31), which were further digested with SfI and cloned into the pComb3X vector. Recombinant phage DNAs were transformed into E. coli ER2738 strain by electroporation (MicroPulser from Bio-Rad). The production of recombinant phages was initiated by the addition of wild-type VCS-M13 helper phage, which were subsequently precipitated with 4% polyethylene glycol 8000 (Sigma, MO, USA) and 3% NaCl (w/v), and finally re-suspended in 1× phosphate-buffered saline (PBS). Then, $10^{10}$~$10^{11}$ plaque-forming units (pfu) of recombinant phages in the scFv antibody libraries were added to wells pre-coated with purified CAIX protein (0.25 g/well) and incubated at 37° C. for 2 hrs. After removing the unbound phages, bound phages were eluted with His-elusion buffer (pH=2.2), neutralized with 2 M Tris base buffer (pH=9.1) and used to infect the E. coli ER2738 strain. The amplified phages were precipitated and recovered as described above for the next round of selection. After $4^{th}$ biopanning, total phagemid DNA from E. coli ER2738 was purified. A panel of randomly selected clones was cultured overnight, diluted 100× in super broth containing 1 mM $MgCl_2$ and ampicillin (50 g/ml) and further grown for 8 h. After induction with 1 mM isopropyl-β-D-thiogalactopyranoside (IPTG) overnight, the bacteria were harvested through centrifugation, resuspended in histidine (His)-binding buffer (20 mM sodium phosphate, 0.5 M NaCl, 20 mM sodium phosphate, 6M urea, pH7.4), and lysed by sonication. The scFv antibodies were purified using $Ni^{2+}$-charged Sepharose (GE Healthcare Bio-Sciences AB, Sweden) according to the manufacturer's instructions.

Western Blotting

The purified recombinant CAIX protein or cell lysates were subjected to SDS-PAGE analysis and transferred onto nitrocellulose membranes (Amersham Biosciences, UK). After blocked with 5% skim milk in TBST for 1 hr, the anti-CAIX IgY from $5^{th}$ immunized chicken (1: 5,000-8,000) or bacterial supernatants containing anti-CAIX scFv antibody (1:10) or purified anti-CAIX scFv antibodies (10 μg/ml) were added and incubated for 1 hr at room temperature. After vigorous washings, horseradish peroxidase (HRP)-conjugated polyclonal donkey anti-chicken IgY antibodies (1:10,000) (Jackson ImmunoResearch, PA, USA) were added and incubated for an additional 1 hr for detecting the bound IgY antibodies. Besides, mouse anti-HA tag mAb (1:3,000-5,000), followed by RP-conjugated rabbit anti-mouse antibodies (1:5,000-10,000), were used for detecting the bound scFv antibodies. After washings as above, the membranes were developed with diaminobenzidine (DAB) or ECL substrate. The ImageQuant LAS4500 was used for ECL intensity detection.

ELISA and Competitive ELISA

To examine their binding reactivity, a series of diluted IgY antibodies (500-256,000 fold) purified from chicken after $5^{th}$ immunization or supernatants of anti-CAIX scFv antibodies (1:10) or purified anti-scFv antibodies (1 μg/ml) were incubated with the purified CAIX proteins (0.25 μg/well) immobilized on ELISA plate wells. After vigorous washings, the bound IgY antibodies were detected by adding HRP-conjugated polyclonal donkey anti-chicken IgY antibodies (1:10,000) (Jackson ImmunoResearch, PA, USA) while the bound CAIX scFv antibodies were detected by mouse anti-HA mAb (1:3,000-5,000), followed by HRP-conjugated rabbit anti-mouse (1:5,000-10,000). After washing as above, a tetramethylbenzidine (TMB) substrate solution (Sigma, USA) was added to the wells for color development. The reaction was stopped with 1 N HCl and the optical density was measured at 450 nm using an ELISA plate reader (BioTek Synergy HT). Dissociate constant ($K_d$) was calculated according to the published protocols (Friguet et al. J. Immunol. Methods, 77: 305-319, 1985)

For the competitive ELISA, CAIX fragment proteins (200-0 g/ml) were first mixed with equal volume of CAIX scFv antibodies (1 g/ml) for 1 hr at 37° C. or at 4° C. overnight and added to the plates coated with purified CAIX proteins for detecting the binding specificity. The bound CAIX scFv antibodies were detected by mouse anti-HA mAb (1:5,000), followed by HRP-conjugated rabbit anti-mouse IgG (1:10,000). After washing as above, a tetramethylbenzidine (TMB) substrate solution (Sigma, USA) was added to the wells for color development. The reaction was stopped with HCl and the optical density was measured at 450 nm using an ELISA plate reader (BioTek Synergy HT). The ELISA tests were carried out in the duplicated wells for each sample. ELISA data were presented as mean±SD of the duplicated experiments.

Example 1 Analysis of Purified Anti-CAIX scFvs (NAVICA9S1, NAVICA9S2, NAVICA9L1, NAVICA9L2 and NAVICA9L3) and Recombinant CAIX Proteins The SDS-PAGE was stained with coomassie blue dye and shown below. NAVICA9S1 (Lane 1), NAVICA9S2 (Lane 2), NAVICA9L1 (Lane 3), NAVICA9L2 (Lane 4) and NAVICA9L3 (Lane 5) were purified according to the above-mentioned methods (FIG. 1 (A)). The recombinant CAIX proteins (ECD) and F3 were also purified and shown in FIG. 1 (B). FIG. 1 (C) shows the full length, extra-cellular domain (ECD), fragment 1 (F1), fragment 2 (F2) and fragment 3 (F3) of CAIX.

Example 2 Binding Ability of Anti-CAIX scFvs Analyzed by Western Blot

Figure 2:
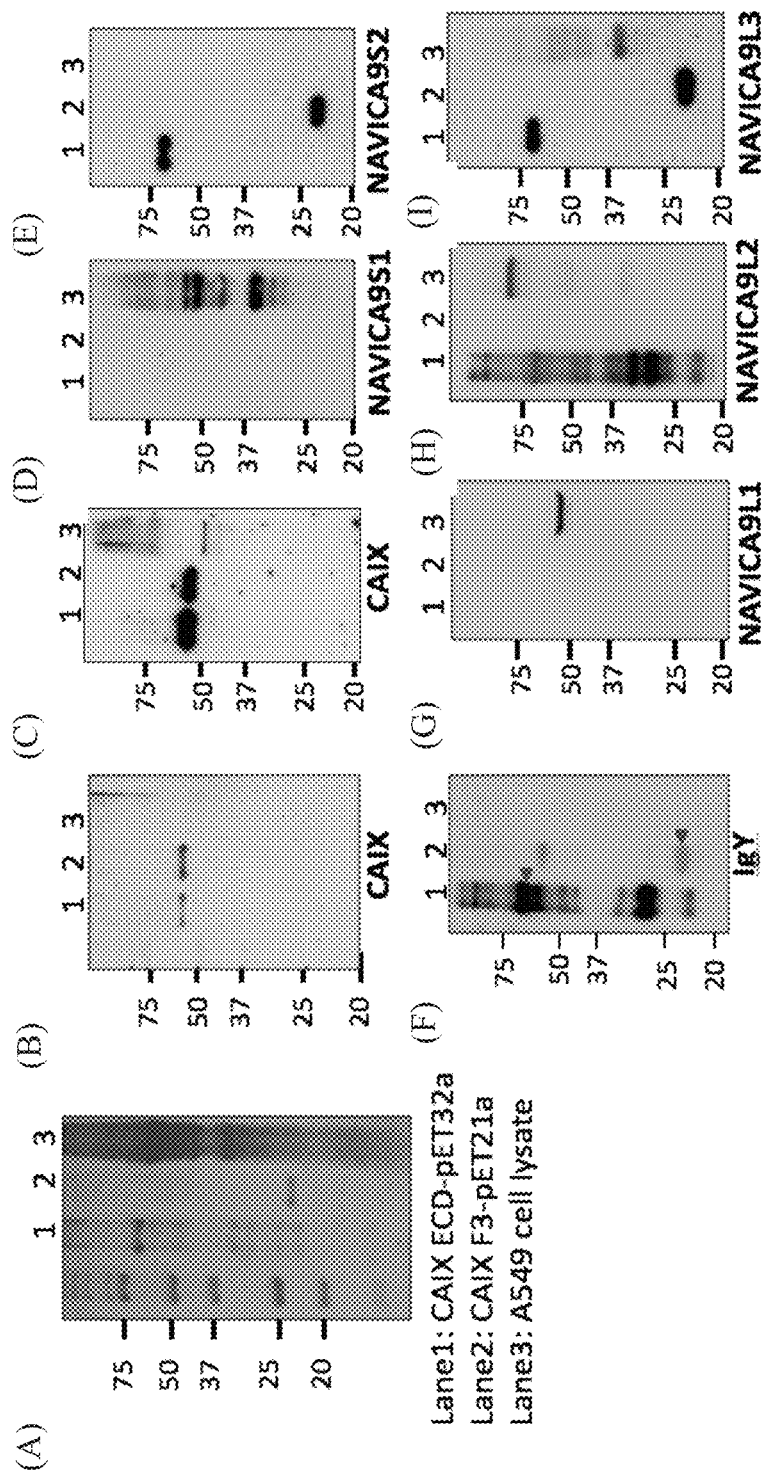
FIG. 2 (A) shows the location of CAIX proteins and A549 cell lysate on the SDS-PAGE. Figure (B) to (I) show the binding ability of anti-CAIX antibody or scFv by western blot. (B), mouse anti-CAIX Ab; (C), mouse anti-CAIX Ab; (D), NAVICA9S1; (E), NAVICA9S2; (F), IgY; (G), NAVICA9L1; (H), NAVICA9L2; and (I) NAVICA9L3.

Recombinant CAIX ECD (lane 1), F3 fragment (lane 2) and A549 cell lysate (lane 3) were visualized on SDS-PAGE (FIG. 2A). Accordingly, the same amount of proteins on duplicated SDS-PAGE was transferred onto nitrocellulose membrane (NC). After blocked for one hour, mouse anti-CAIX IgG (1:2,000) (ab107257) or chicken anti-CAIX IgY (1:5,000) were added to the NC as the primary antibodies. After one-hour reaction, the NC was washed with PBST for 3 times. After washing, the HRP-conjugated rabbit anti-mouse IgG (1:10,000) or HRP-conjugated donkey anti-IgY (1:10,000) were added to the NC. After one-hour reaction, the NC was washed with PBST and incubated with ECL solution. Similarly, the anti-CAIX scFv monoclonal antibodies (10 μl/ml) were added to NC as the primary antibodies. Then the mouse anti-HA IgG and HRP-conjugated rabbit anti-mouse IgG were sequentially added as the secondary and the third antibodies. After incubated with ECL, the binding activity was detected and shown in FIG. 2.

Example 3 Binding Ability of Anti-CAIX scFvs Analyzed by ELISA

Figure 3:
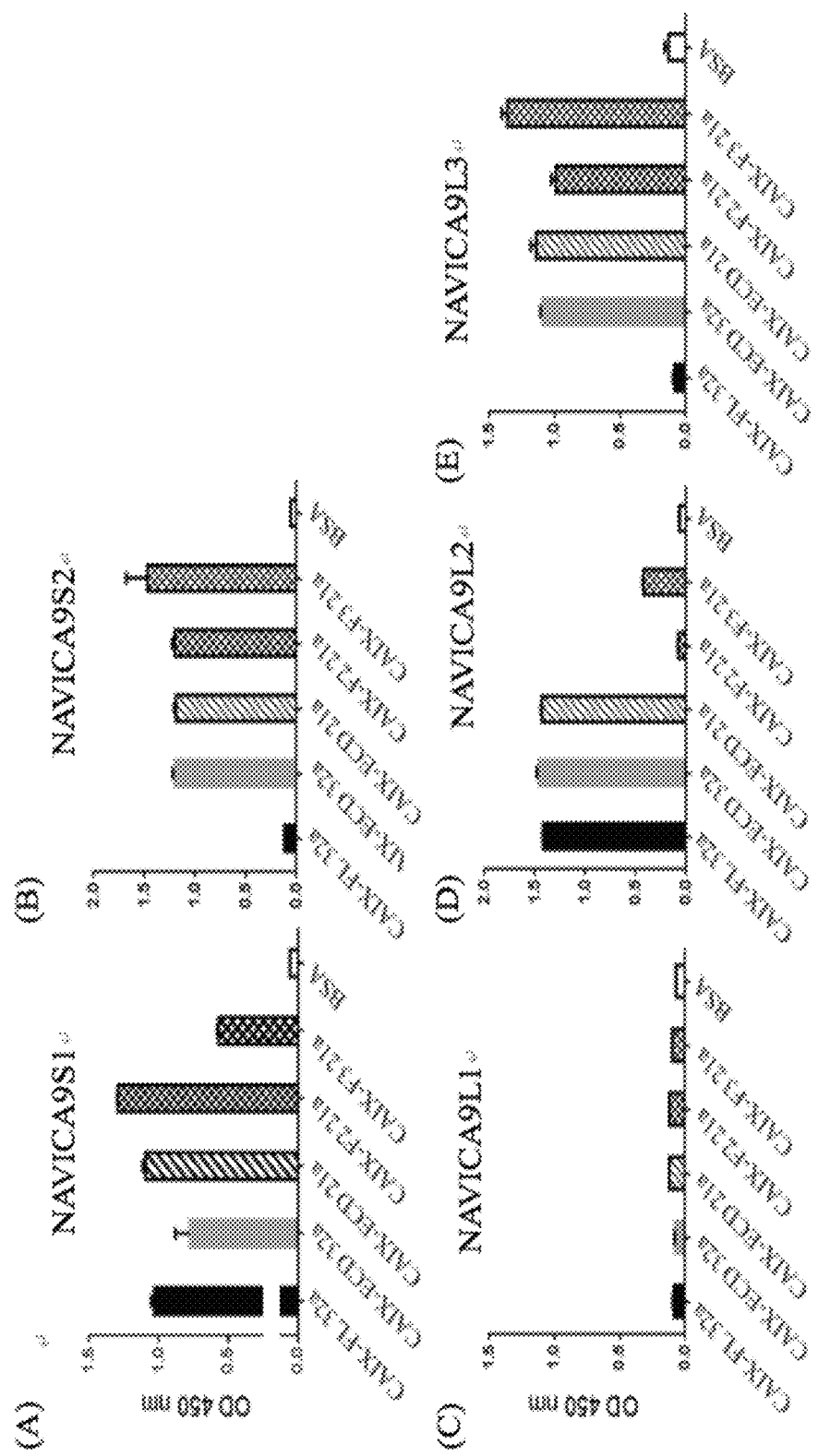
FIGS. 3 (A) to (E) show the binding affinity of anti-CAIX monoclonal scFv of (A) NAVICA9S1, (B) NAVICA9S2, (C) NAVICA9L1, (D) NAVICA9L2 and (E) NAVICA9L3.
Figure 4:
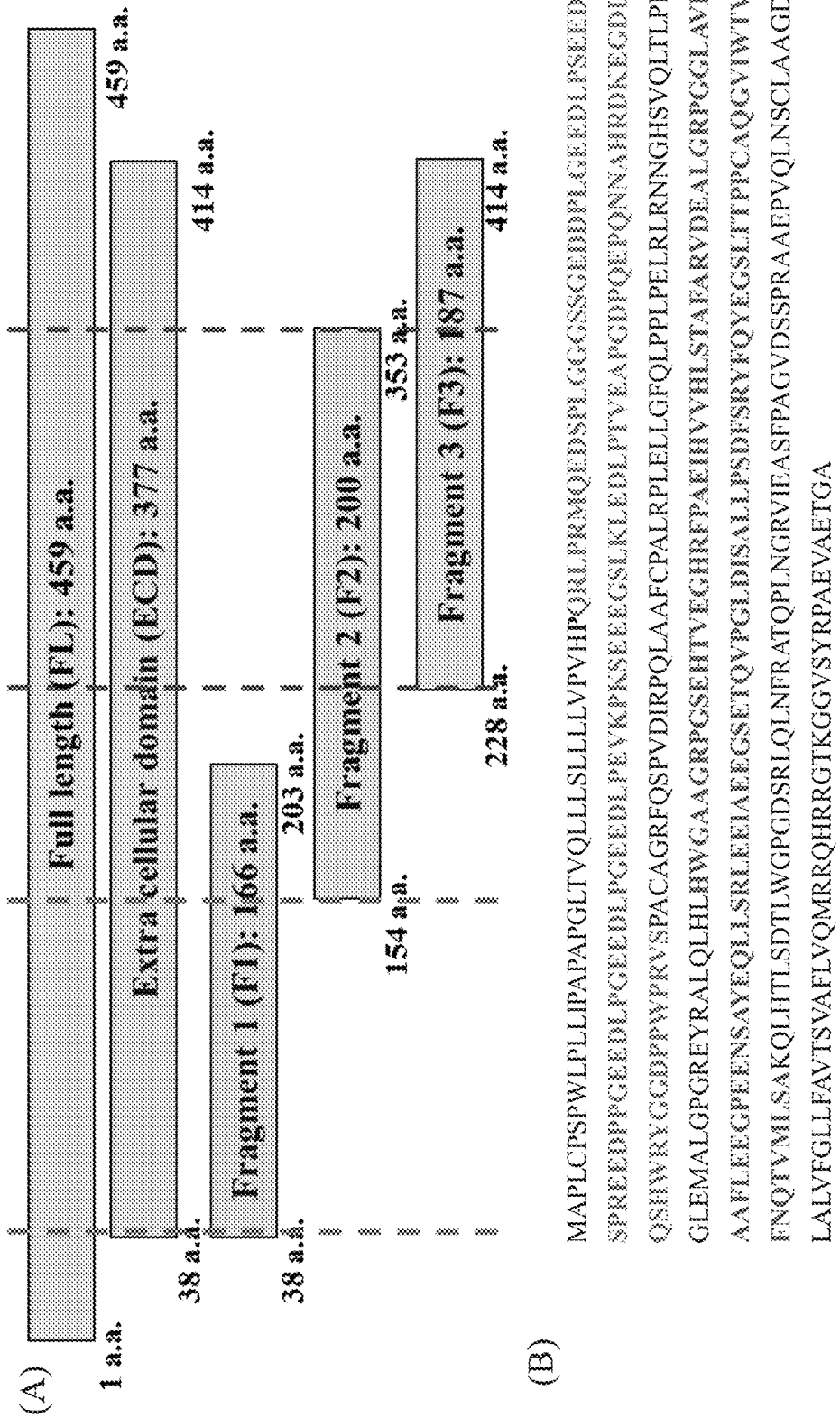
FIGS. 4 (A) and (B) show that (A) the clone NAVICA9S1, NAVICA9S2 and NAVICA9L3 bind to the CAIX FL, ECD, F2 and F3 fragments and the clone NAVICA9L2 binds to the CAIX FL and ECD, but not F2 and F3 fragments and (B) two epitopes locates between 38 to 153 amino acid and between 228 and 353 amino acid, respectively.

The recombinant CAIX-FL, ECD, ECD, F2 and F3 (either expressed in pET32a or pET21a) were attached to a 96 half-well ELISA plate at a concentration of 0.25 μg/well. After one-hour incubation, the unbound proteins were removed and 5% PBS-milk was added for blocking. After one-hour reaction, the PBS-milk was removed and each of the anti-CAIX antibodies (1 µg/ml) was added. After washed with PBST, the mouse anti-HA IgG (1:5,000) and the HRP-conjugated rabbit anti-mouse IgG (1:10,000) were sequentially added to the plate. Then, 3,3',5,5'-tetramethylbenzidine (TMB) was added for color development, which was stopped by HCl and detected using an ELISA plate reader. The results were shown in FIG. 3.

Example 4 Epitope Mapping

To define the antigenic epitopes on CAIX protein, the purified anti-CAIX antibodies were examined for their binding to recombinant CAIX fragments. The results showed NAVICA9S1, NAVICA9S2 and NAVICA9L3 recognized CAIX FL, ECD, F2 and F3 fragments, suggesting that the epitope is located between amino acid residues 228 to 353. Clone NAVICA9L2 recognized CAIX FL and ECD but not F2 and F3 fragments, suggesting that the epitope is located between amino acids 38 to 153.

Example 5 Estimated Dissociation Constant of Anti-CAIX scFvs by Competitive ELISA To determine the binding affinity of the anti-CAIX scFvs, competitive ELISA was performed. The CAIX ECD fragment proteins in 2-fold serial dilution (100-13 µg/ml) were pre-incubated with anti-CAIX scFvs (NAVICA9S1: 0.62 µg/ml, NAVICA9S2: 0.32 µg/ml, NAVICA9L2: 0.16 µg/ml, NAVICA9L3: 0.32 µg/ml) at 1:1 volume ratio at room temperature for 1 hour. The mixtures were then added into ELISA plate coated with CAIX ECD fragment proteins (0.25 or 0.5 µg/well). After 1 hour incubation, the mouse anti-HA IgG (1:5,000) and HRP-conjugated rabbit anti-mouse IgG (1:10,000) were added as the secondary and third antibodies. Following the incubation and washing, 3,3',5,5'-Tetramethylbenzidine (TMB) was added for color development, which was stopped by HCl and detected using an ELISA plate reader. The $K_d$ values of scFvs were estimated and expressed by molarity (M) as described by Friguet et al. (J. Immunol. Methods, 77: 305-319, 1985). N/A: not available. The dissociation constants of anti-CAIX monoclonal scFv are shown in Table 1 below.

TABLE 1

| Anti-CAIX scFv | Dissociation constant |
|---|---|
| NAVICA9S1 | $6.43 \times 10^{-8}$ M |
| NAVICA9S2 | $1.15 \times 10^{-8}$ M |
| NAVICA9L1 | N/A |
| NAVICA9L2 | $1.40 \times 10^{-7}$ M |
| NAVICA9L3 | $9.26 \times 10^{-9}$ M |

Example 6 Flow Cytometry Assay

Figure 5A:
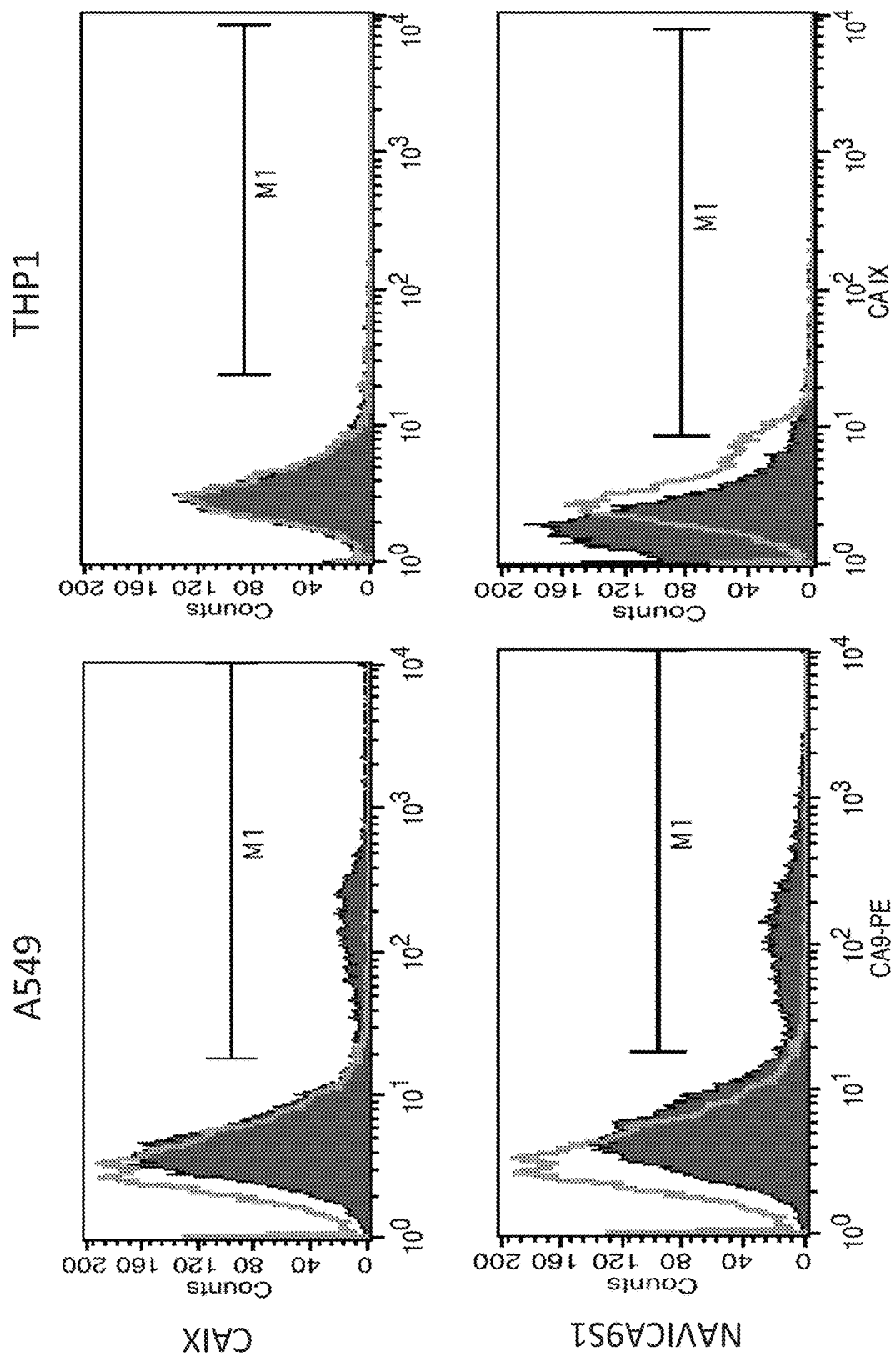
FIG. 5 shows the flow cytometry of anti-CAIX scFvs and anti-CAIX (abcam, ab107257) against A549 cells or THP-1 cells.
Figure 5B:
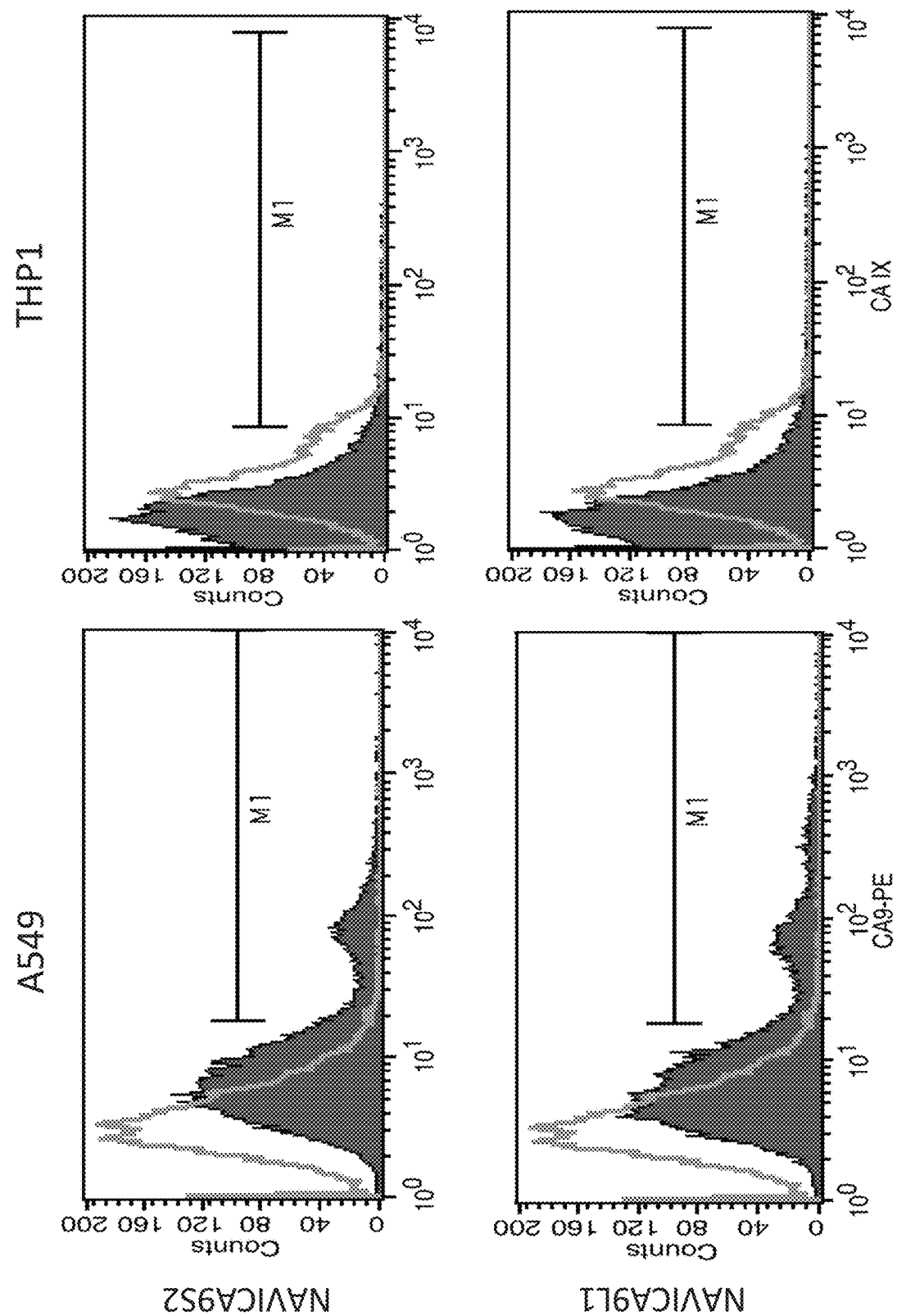
Figure 5C:
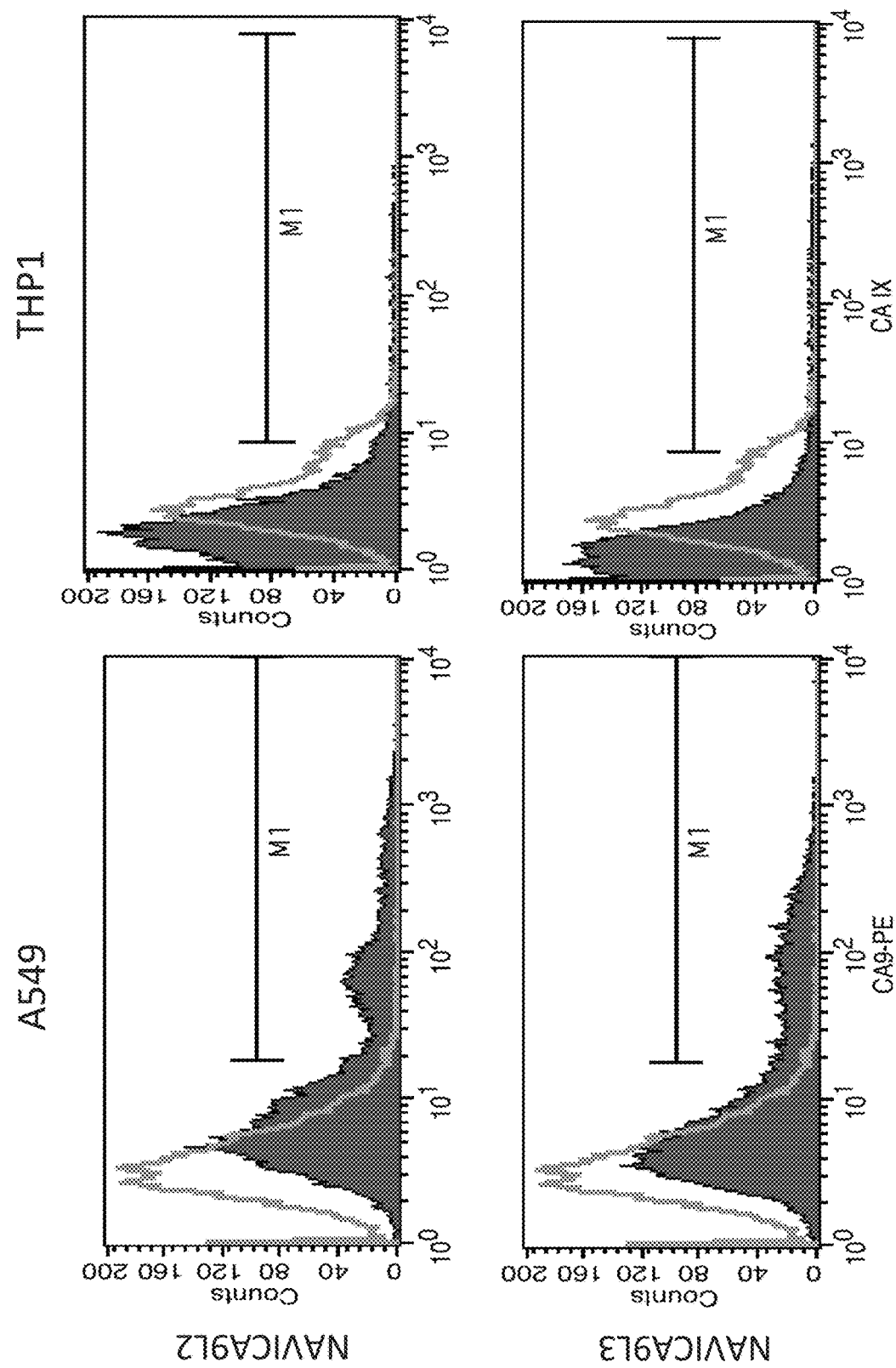

The anti-CAIX scFvs and anti-CAIX (abcam, ab107257) were incubated with $2 \times 10^5$ A549 cells (CAIX+) or THP-1 cells (CAIX−) at 4° C. for 20 minutes. Mouse anti-HA IgG and PE-conjugated anti-mouse IgG were added as the secondary and third antibodies; PE-conjugated anti-mouse IgG also were added as the secondary antibody of anti-CAIX antibodies (abcam, ab107257). After washing, the cells were subjected to the flow cytometry assay and the results are shown in FIG. 5.

What is claimed is:

1. An isolated anti-carbonic anhydrase IX (CAIX) antibody or antigen-binding portion thereof, comprising:
   a light chain complementarity determining region 1 (L-CDR1) of SEQ ID NO:4; a light chain CDR2 (L-CDR2) of SEQ ID NO:5; and a light chain CDR3 (L-CDR3) of SEQ ID NO:3; and
   a heavy chain CDR1 (H-CDR1) of SEQ ID NO:12; a heavy chain CDR2 (H-CDR2) of SEQ ID NO:13; and a heavy chain CDR3 (H-CDR3) of SEQ ID NO:14; such that said isolated antibody or antigen-binding portion thereof binds to CAIX.

2. The isolated anti-CAIX antibody or antigen-binding portion thereof of claim 1, wherein the antibody is a monoclonal antibody, chimeric antibody, or humanized antibody.

3. The isolated anti-CAIX antibody or antigen-binding portion thereof of claim 1, which comprises a constant region and one or more heavy and light chain variable framework regions of a human antibody sequence.

4. The isolated anti-CAIX antibody or antigen-binding portion thereof of claim 3, which comprises up to 10 amino acid substitutions in the framework regions.

5. The isolated anti-CAIX antibody or antigen-binding portion thereof of claim 3, which comprises framework regions of Avastin.

6. The isolated anti-CAIX antibody or antigen-binding portion thereof of claim 3, wherein the framework regions comprise L-FR1 having an amino acid sequence of SEQ ID NO: 34, L-FR2 having an amino acid sequence of SEQ ID No: 38, L-FR3 having an amino acid sequence of SEQ ID NO: 41 and L-FR4 having an amino acid sequence of SEQ ID NO: 44 and H-FR1 having an amino acid sequence of SEQ ID NO: 47, H-FR2 having an amino acid sequence of SEQ ID NO: 54, H-FR3 having an amino acid sequence of SEQ ID NO: 58 and H-FR4 having an amino acid sequence of SEQ ID NO:64.

7. The isolated anti-CAIX antibody or antigen-binding portion thereof of claim 1, wherein the light chain comprises an amino acid sequence having a sequence as set forth in SEQ ID NO: 22.

8. The isolated anti-CAIX antibody or antigen-binding portion thereof of claim 1, wherein the heavy chain comprises an amino acid sequence having a sequence as set forth in SEQ ID NO: 25; or an antigen-binding portion thereof.

9. The isolated anti-CAIX antibody or antigen-binding portion thereof of claim 1, which comprises a light chain having an amino acid sequence as set forth in SEQ ID NO: 22 and a heavy chain having an amino acid sequence as set forth in SEQ ID NO: 25.

10. The isolated anti-CAIX antibody or antigen-binding portion thereof of claim 1, wherein the antigen-binding portion is Fab, F(ab')2, Fd, Fv, dAb or scFv.

11. A pharmaceutical composition comprising the isolated anti-CAIX antibody or antigen-binding portion thereof of claim 1 and a pharmaceutically acceptable carrier or excipient.

12. The pharmaceutical composition of claim 11, which further comprises one or more additional anti-cancer drug.

13. A method for treating cancer in a subject comprising administering the isolated anti-CAIX antibody or antigen-binding portion thereof of claim 4 to the subject.

14. The method of claim 13, which further comprises a step of administering one or more additional anti-cancer drugs concurrently, subsequently, or separately with the isolated anti-CAIX antibody or antigen-binding portion thereof of claim 1.

15. A single chain variable fragment (scFv) that binds CAIX, comprising:
   a) a light chain variable region of a light chain having an amino acid sequence as set forth in the sequence of SEQ ID NO: 22;
   b) a linker; and
   c) a heavy chain variable region of a heavy chain having an amino acid sequence as set forth in the sequence of SEQ ID NO: 25.

16. The scFv of claim 15, wherein the linker is a peptide linker.

17. The scFv of claim 15, wherein the linker comprises 4-20 amino acids.

18. The scFv of claim 15, wherein the linker comprises a peptide having an amino acid sequence of SEQ ID NO:29, 30 or 31.

* * * * *

UNITED STATES PATENT AND TRADEMARK OFFICE
CERTIFICATE OF CORRECTION

Page 1 of 1

PATENT NO. : 12,351,645 B2
APPLICATION NO. : 17/051635
DATED : July 8, 2025
INVENTOR(S) : Bor-Yu Tsai and Wei-Ting Hsu It is certified that error appears in the above-identified patent and that said Letters Patent is hereby corrected as shown below:

On the Title Page

Under (73) Assignee please correct the spelling of the applicant by deleting "NAVI BIO-THERAPEUTICIS, INC." and adding NAVI BIO-THERAPEUTICS, INC.

Signed and Sealed this
Eighteenth Day of November, 2025

John A. Squires
*Director of the United States Patent and Trademark Office*